US010159600B2

United States Patent
Horvath et al.

(10) Patent No.: US 10,159,600 B2
(45) Date of Patent: Dec. 25, 2018

(54) ADJUSTABLE INTRAOCULAR FLOW REGULATION

(71) Applicant: AqueSys, Inc., Aliso Viejo, CA (US)

(72) Inventors: Christopher Horvath, Mission Viejo, CA (US); Laszlo O. Romoda, San Clemente, CA (US); Brian Hamstrom, Trabuco Canyon, CA (US); Ronald D. Bache, Mission Viejo, CA (US); Guenther Grabner, Salzburg (AT); Herbert A. Reitsamer, Salzburg (AT)

(73) Assignee: AqueSys, Inc., Aliso Viejo, CA (US)

( * ) Notice: Subject to any disclaimer, the term of this patent is extended or adjusted under 35 U.S.C. 154(b) by 103 days.

(21) Appl. No.: 13/771,000

(22) Filed: Feb. 19, 2013

(65) Prior Publication Data

US 2014/0236066 A1  Aug. 21, 2014

(51) Int. Cl.
  *A61F 9/007* (2006.01)
  *A61L 31/08* (2006.01)
  *A61L 31/16* (2006.01)

(52) U.S. Cl.
  CPC .......... *A61F 9/00781* (2013.01); *A61L 31/08* (2013.01); *A61L 31/16* (2013.01)

(58) Field of Classification Search
  CPC .................. A61F 2009/00891; A61F 9/00781
  USPC ............................................................ 604/9
  See application file for complete search history.

(56) References Cited

U.S. PATENT DOCUMENTS

| 3,788,327 | A | 1/1974 | Donowitz et al. |
| 3,960,150 | A | 6/1976 | Hussain et al. |
| 4,090,530 | A | 5/1978 | Lange |
| 4,431,688 | A | 2/1984 | Kornmann |
| 4,562,463 | A | 12/1985 | Lipton |
| 4,583,117 | A | 4/1986 | Lipton et al. |
| 4,722,724 | A | 2/1988 | Schocket |
| 4,744,362 | A | 5/1988 | Grundler |
| 4,750,901 | A | 6/1988 | Molteno |
| 4,787,885 | A | 11/1988 | Binder |

(Continued)

FOREIGN PATENT DOCUMENTS

| GB | 2 296 663 A | 7/1996 |
| WO | WO 94/13234 A1 | 6/1994 |

(Continued)

OTHER PUBLICATIONS

Arnold G. Coran, Anthony Caldamone, N. Scott Adzick, Thomas M. Krummel, Jean-Martin Laberge, Robert Shamberger, "Pediatric Surgery", Feb. 14, 2012, Elsevier Saunders, vol. 2 7th Edition, p. 1683.*

(Continued)

*Primary Examiner* — Tatyana Zalukaeva
*Assistant Examiner* — Kai Weng
(74) *Attorney, Agent, or Firm* — Nathan S. Smith; Danny Mansour; Morgan, Lewis & Bockius LLP

(57) ABSTRACT

Methods and devices for adjusting or configuring the flow rate of an intraocular shunt are provided whereby hypotony can be avoided by increasing the flow rate through the device. In some embodiments, the device is a shunt that can have a first flow that can be modified to a second flow by modifying the shunt, such as by cutting the shunt. Additionally, one or more dissolvable portions can be present to provide an initial flow restriction and subsequent increase in flow over time.

24 Claims, 12 Drawing Sheets

(56) References Cited

U.S. PATENT DOCUMENTS

| | | |
|---|---|---|
| 4,804,382 A | 2/1989 | Turina et al. |
| 4,820,626 A | 4/1989 | Williams et al. |
| 4,826,478 A | 5/1989 | Schocket |
| 4,848,340 A | 7/1989 | Bille et al. |
| 4,863,457 A | 9/1989 | Lee |
| 4,902,292 A | 2/1990 | Joseph |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,178,604 A | 1/1993 | Baerveldt et al. |
| 5,180,362 A | 1/1993 | Worst |
| 5,201,750 A | 4/1993 | Hocherl et al. |
| 5,275,622 A | 1/1994 | Lazarus et al. |
| 5,290,295 A | 3/1994 | Querals et al. |
| 5,300,020 A | 4/1994 | L'Esperance, Jr. |
| 5,338,291 A | 8/1994 | Speckman et al. |
| 5,342,370 A | 8/1994 | Simon et al. |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,476,445 A | 12/1995 | Baerveldt et al. |
| 5,516,522 A | 5/1996 | Peyman et al. |
| 5,520,631 A | 5/1996 | Nordquist et al. |
| 5,545,206 A | 8/1996 | Carson |
| 5,558,629 A | 9/1996 | Baerveldt et al. |
| 5,558,630 A | 9/1996 | Fisher |
| 5,601,094 A | 2/1997 | Reiss |
| 5,665,093 A | 9/1997 | Atkins et al. |
| 5,665,114 A | 9/1997 | Weadock et al. |
| 5,670,161 A | 9/1997 | Healy et al. |
| 5,688,562 A | 11/1997 | Hsiung |
| 5,695,474 A | 12/1997 | Daugherty |
| 5,704,907 A | 1/1998 | Nordquist et al. |
| 5,722,948 A | 3/1998 | Gross |
| 5,743,868 A | 4/1998 | Brown et al. |
| 5,763,491 A | 6/1998 | Brandt et al. |
| 5,868,697 A | 2/1999 | Richter et al. |
| 5,908,449 A | 6/1999 | Bruchman et al. |
| 5,928,424 A | 7/1999 | Krebs et al. |
| 5,932,299 A | 8/1999 | Katoot |
| 6,007,511 A | 12/1999 | Prywes |
| 6,007,578 A | 12/1999 | Schachar |
| 6,050,970 A | 4/2000 | Baerveldt |
| 6,102,045 A | 8/2000 | Nordquist et al. |
| 6,165,210 A | 12/2000 | Lau et al. |
| 6,203,513 B1 | 3/2001 | Yaron et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,666,841 B2 | 12/2003 | Gharib et al. |
| 6,676,998 B2 | 1/2004 | Huang et al. |
| 6,699,210 B2 | 3/2004 | Williams et al. |
| 6,726,664 B2 | 4/2004 | Yaron et al. |
| 6,730,056 B1 | 5/2004 | Ghaem et al. |
| 6,736,791 B1 | 5/2004 | Tu et al. |
| 6,881,198 B2 | 4/2005 | Brown |
| 6,939,298 B2 | 9/2005 | Brown et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,980 B2 | 4/2007 | Christian et al. |
| 7,291,125 B2 | 11/2007 | Coroneo |
| 7,297,154 B2 | 11/2007 | Tu et al. |
| 7,331,984 B2 | 2/2008 | Tu et al. |
| 7,344,528 B1 | 3/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,488,303 B1 | 2/2009 | Haffner et al. |
| 7,524,298 B2 | 4/2009 | Gharib et al. |
| 7,594,899 B2 | 9/2009 | Pinchuk et al. |
| 7,625,384 B2 | 12/2009 | Eriksson et al. |
| 7,678,065 B2 | 3/2010 | Haffner et al. |
| 7,708,711 B2 | 5/2010 | Tu et al. |
| 7,717,872 B2 * | 5/2010 | Shetty .............. A61F 9/00781 604/264 |
| 7,740,604 B2 | 6/2010 | Schieber et al. |
| 7,794,437 B2 | 9/2010 | Humayun et al. |
| 7,837,644 B2 | 11/2010 | Pinchuk et al. |
| 7,862,531 B2 | 1/2011 | Yaron et al. |
| 7,867,186 B2 | 1/2011 | Haffner et al. |
| 7,998,497 B2 | 8/2011 | de Juan, Jr. et al. |
| 8,003,124 B2 | 8/2011 | Varner et al. |
| 8,109,896 B2 | 2/2012 | Nissan et al. |
| 8,267,882 B2 | 9/2012 | Euteneuer et al. |
| 8,277,437 B2 | 10/2012 | Saal et al. |
| 8,308,701 B2 | 11/2012 | Horvath et al. |
| 8,313,454 B2 | 11/2012 | Yaron et al. |
| 8,337,393 B2 | 12/2012 | Silvestrini et al. |
| 8,337,509 B2 | 12/2012 | Schieber et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,486,000 B2 | 7/2013 | Coroneo |
| 8,506,515 B2 | 8/2013 | Burns et al. |
| 8,512,404 B2 | 8/2013 | Frion et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,113,994 B2 | 8/2015 | Romoda et al. |
| 9,125,723 B2 | 9/2015 | Horvath et al. |
| 2002/0099434 A1 | 7/2002 | Buscemi et al. |
| 2002/0115966 A1 * | 8/2002 | Christensen ...... A61M 5/16804 604/264 |
| 2002/0133168 A1 | 9/2002 | Smedley et al. |
| 2002/0143284 A1 | 10/2002 | Tu et al. |
| 2003/0015203 A1 | 1/2003 | Makower et al. |
| 2003/0055372 A1 | 3/2003 | Lynch et al. |

(56) References Cited

U.S. PATENT DOCUMENTS

| | | |
|---|---|---|
| 2003/0060752 A1 | 3/2003 | Bergheim et al. |
| 2003/0097053 A1 | 5/2003 | Itoh |
| 2003/0097151 A1 | 5/2003 | Smedley et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0077987 A1 | 4/2004 | Rapacki et al. |
| 2004/0111050 A1 | 6/2004 | Smedley et al. |
| 2004/0147870 A1 | 7/2004 | Burns et al. |
| 2004/0154946 A1 | 8/2004 | Solovay et al. |
| 2004/0210209 A1 | 10/2004 | Yeung et al. |
| 2004/0216749 A1 | 11/2004 | Tu |
| 2004/0225250 A1 | 11/2004 | Yablonski |
| 2004/0254521 A1 | 12/2004 | Simon |
| 2004/0260227 A1 | 12/2004 | Lisk, Jr. et al. |
| 2005/0049578 A1 | 3/2005 | Tu et al. |
| 2005/0101967 A1 | 5/2005 | Weber |
| 2005/0119601 A9 | 6/2005 | Lynch et al. |
| 2005/0143363 A1 | 6/2005 | De Juan et al. |
| 2005/0246023 A1 | 11/2005 | Yeung |
| 2005/0250788 A1 | 11/2005 | Tu et al. |
| 2005/0261624 A1 | 11/2005 | Wilcox |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0032507 A1 | 2/2006 | Tu |
| 2006/0106370 A1 | 5/2006 | Baerveldt et al. |
| 2006/0110428 A1 | 5/2006 | De Juan et al. |
| 2006/0116625 A1 | 6/2006 | Renati et al. |
| 2006/0147643 A1 | 6/2006 | Volkov et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0200113 A1 | 9/2006 | Haffner et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | de Juan, Jr. et al. |
| 2007/0233037 A1 | 10/2007 | Gifford et al. |
| 2007/0269487 A1 | 11/2007 | de Juan, Jr. et al. |
| 2007/0293807 A1 | 12/2007 | Lynch et al. |
| 2007/0293872 A1 | 12/2007 | Peyman |
| 2008/0057106 A1 | 3/2008 | Erickson et al. |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0082860 A1 | 3/2009 | Schieber et al. |
| 2009/0082862 A1 | 3/2009 | Schieber et al. |
| 2009/0099626 A1 | 4/2009 | de Juan, Jr. et al. |
| 2009/0104243 A1 | 4/2009 | Utkhede et al. |
| 2009/0177138 A1 | 7/2009 | Brown et al. |
| 2009/0182421 A1 | 7/2009 | Silvestrini et al. |
| 2009/0209910 A1 | 8/2009 | Kugler et al. |
| 2009/0287136 A1 | 11/2009 | Castillejos |
| 2010/0098772 A1 | 4/2010 | Robinson et al. |
| 2010/0100104 A1 | 4/2010 | Yu et al. |
| 2010/0114006 A1 | 5/2010 | Baerveldt |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0191103 A1 | 7/2010 | Stamper et al. |
| 2010/0241046 A1 | 9/2010 | Pinchuk et al. |
| 2010/0249691 A1* | 9/2010 | Van Der Mooren et al. .... 604/9 |
| 2011/0046536 A1 | 2/2011 | Stegmann et al. |
| 2011/0098627 A1 | 4/2011 | Wilcox |
| 2011/0098809 A1 | 4/2011 | Wardle et al. |
| 2011/0105986 A1 | 5/2011 | Bronstein et al. |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2011/0319806 A1 | 12/2011 | Wardle |
| 2012/0078362 A1 | 3/2012 | Haffner et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0226150 A1 | 9/2012 | Balicki et al. |
| 2012/0310137 A1 | 12/2012 | Silvestrini |
| 2012/0323159 A1 | 12/2012 | Wardle et al. |
| 2013/0149429 A1 | 6/2013 | Romoda et al. |
| 2013/0150770 A1 | 6/2013 | Horvath et al. |
| 2013/0150773 A1 | 6/2013 | Hertz et al. |
| 2013/0184631 A1 | 7/2013 | Pinchuk |
| 2013/0245573 A1 | 9/2013 | de Juan, Jr. et al. |
| 2013/0253406 A1 | 9/2013 | Horvath et al. |
| 2013/0253528 A1 | 9/2013 | Haffner et al. |
| 2013/0281817 A1 | 10/2013 | Schaller et al. |
| 2013/0281907 A1 | 10/2013 | Wardle et al. |
| 2013/0289467 A1 | 10/2013 | Haffner et al. |
| 2013/0325024 A1 | 12/2013 | Nissan et al. |
| 2014/0018720 A1 | 1/2014 | Horvath et al. |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0163448 A1 | 6/2014 | Lind et al. |
| 2014/0180189 A1 | 6/2014 | Horvath et al. |
| 2014/0213958 A1 | 7/2014 | Clauson et al. |
| 2014/0236065 A1 | 8/2014 | Romoda et al. |
| 2014/0236066 A1 | 8/2014 | Horvath et al. |
| 2014/0236067 A1 | 8/2014 | Horvath et al. |
| 2014/0243730 A1 | 8/2014 | Horvath et al. |
| 2014/0272102 A1 | 9/2014 | Romoda et al. |
| 2014/0275923 A1 | 9/2014 | Haffner et al. |
| 2014/0276332 A1 | 9/2014 | Crimaldi et al. |
| 2014/0287077 A1 | 9/2014 | Romoda et al. |
| 2014/0303544 A1 | 10/2014 | Haffner et al. |
| 2014/0323995 A1 | 10/2014 | Clauson et al. |
| 2014/0364789 A1 | 12/2014 | Schaller |
| 2015/0005689 A1 | 1/2015 | Horvath et al. |
| 2015/0011926 A1 | 1/2015 | Reitsamer et al. |
| 2015/0038893 A1 | 2/2015 | Haffner et al. |
| 2015/0045714 A1 | 2/2015 | Horvath et al. |
| 2015/0057591 A1 | 2/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0256321 A1 | 9/2016 | Horvath et al. |
| 2016/0256322 A1 | 9/2016 | Horvath et al. |
| 2017/0172800 A1 | 6/2017 | Romoda et al. |

FOREIGN PATENT DOCUMENTS

| | | |
|---|---|---|
| WO | WO 94/21205 A1 | 9/1994 |
| WO | WO 95/08310 A1 | 3/1995 |
| WO | WO 98/23237 A1 | 6/1998 |
| WO | WO-00/056255 A1 | 9/2000 |
| WO | WO-2000/056255 | 9/2000 |
| WO | WO 2002/074052 A2 | 9/2002 |

(56) References Cited

FOREIGN PATENT DOCUMENTS

| WO | WO 2007/087061 A2 | 8/2007 |
|---|---|---|
| WO | WO 2008/005873 A1 | 1/2008 |
| WO | WO-2017/040855 A1 | 3/2017 |

OTHER PUBLICATIONS

U.S. Appl. No. 14/541,070, filed Nov. 13, 2014, entitled "Intraocular Shunt Inserter," Horvath et al.
U.S. Appl. No. 14/697,295, filed Apr. 27, 2015, entitled "Shunt Placement Through the Sclera".

\* cited by examiner

ADJUSTABLE INTRAOCULAR FLOW REGULATION

BACKGROUND

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated in a number of different ways. One manner of treatment involves delivery of drugs such as beta-blockers or prostaglandins to the eye to either reduce production of aqueous humor or increase flow of aqueous humor from an anterior chamber of the eye. Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Such fluid flow pathways allow for aqueous humor to exit the anterior chamber.

SUMMARY

The importance of lowering intraocular pressure (IOP) in delaying glaucomatous progression has been well documented. When drug therapy fails, or is not tolerated, surgical intervention is warranted. There are various surgical filtration methods for lowering intraocular pressure by creating a fluid flow-path between the anterior chamber and the subconjunctival tissue. In one particular method, an intraocular shunt is implanted by directing a needle which holds the shunt through the cornea, across the anterior chamber, and through the trabecular meshwork and sclera, and into the subconjunctival space. See, for example, U.S. Pat. No. 6,544,249, U.S. Patent Application Publication No. 2008/0108933, and U.S. Pat. No. 6,007,511, the entireties of which are incorporated herein by reference.

However, existing implantable shunts may not effectively regulate fluid flow from the anterior chamber. Fluid flow through a traditional shunt is passive, from the anterior chamber to a drainage structure of the eye. If fluid flows from the anterior chamber at a rate greater than it can be produced in the anterior chamber, the surgery can result in an undesirably low intraocular pressure in the anterior chamber of the eye. This condition is known as hypotony. Hypotony occurs when the intraocular pressure is generally less than about 6 mmHg. Risks associated with low intraocular pressure and hypotony include blurred vision, collapse of the anterior chamber, and potentially significant damage to the eye. Such risks could require additional surgical intervention to repair. However, if fluid flow from the eye is not great enough, pressure in the anterior chamber will not be relieved, and damage to the optic nerve and the retina may still occur.

Accordingly, some embodiments disclosed herein provide intraocular implants or shunts for draining fluid from an anterior chamber of an eye and methods of use that enable a clinician to selectively adjust or configure the flow rate or flow parameters of an intraocular shunt in order to avoid hypotony while ensuring that adequate pressure relief is provided.

For example, an intraocular implant or shunt can be provided that is configured to conduct fluid at a first nonzero flow that can be modified to a second flow, when the implant is in an eye, by removing part of the implant.

Some implants can be configured to have a first flow that can be changed to a second flow by shortening the length of the implant.

Some implants can be configured to have a first flow that can be changed to a second flow by removing a restrictive section thereof.

In some embodiments, the first flow can be less than the second flow through the implant. Thus, modification, shortening, or removal of a section thereof can increase the flow through the implant.

An eye implant can be provided that conducts fluid at a first nonzero flow rate, modifiable to a second flow rate, when the implant is in an eye, by removing a removable part of the implant residing in the anterior chamber.

The implant can comprise a wall defining a lumen, and the wall can have a variable inner profile. The implant can also comprise a partially restrictive end. For example, the implant can a gelatin tube that is inserted into the lumen, and the gelatin tube can have an inner profile smaller than an inner profile of the implant lumen.

A longitudinal length of some implants can be shortened to modify the first flow. For example, the first flow rate can be increased to the second flow rate when the implant is cut at a first point along the implant. Further, the first flow rate can be increased to a third flow rate when the implant is cut at a second point along the implant.

Some implants or shunts can comprise a hollow body with a clear-through, unobstructive, or unrestrictive main section and a partially obstructive or flow-limiting restrictive section. The first flow of the shunt can be modifiable to the second flow by modifying, shortening, or removing part of the main section and/or the partially restrictive section.

The main section can have an inlet, an outlet, and a wall defining a lumen extending between the inlet and outlet. The inlet can be configured to receive fluid from the anterior chamber. The main section can comprise a wall defining a lumen. The wall can define a first cross-sectional area or profile and can be configured to direct the fluid from the anterior chamber through the inlet toward the outlet such that, when positioned in the eye, fluid is released through the outlet at a location having lower pressure than the anterior chamber. As discussed herein, the location of lower pressure can be, for example, the intra-Tenon space, the subconjunctival space, the episcleral vein, the suprachoroidal space, or Schlemm's canal.

The partially restrictive section can be in fluid communication with the main section. The partially restrictive section can have a second flow cross-sectional area or profile that is less that the first cross-sectional area or profile.

For example, the partially restrictive section can comprise a gelatin tube. The gelatin tube can be inserted into a lumen of the main section and comprise a wall defining a lumen with a smaller cross-sectional area or profile than the main section cross-sectional area or profile.

The shunt can be configured such that the first flow cross-sectional area is generally circular in shape. Further, the partially restrictive section of the shunt can be formed of a separate material from the main section. The partially restrictive section can be dissolvable. For example, the partially restrictive section has a dissolution rate that is different than a dissolution rate of the shunt.

In some embodiments, the shunt can be configured such that the partially restrictive section comprises first and second portions. For example, the first and second portions can be axially spaced apart from each other. The first and second portions can be concentrically layered within the lumen. The first and second portions can also be positioned at opposing ends of the main section. The first and second portions can be dissolvable. For example, the first portion can have a first dissolution rate, and the second portion can have a second dissolution rate that is different from the first dissolution rate.

Additionally, the shunt can be configured such that at least a portion of the body comprises a drug. For example, the partially restrictive section can comprise a drug. Further, the partially restrictive section can comprise a gelatin. The main section can comprise a cross-linked gelatin. Further, the partially restrictive section can comprise a cross-linked gelatin that is cross-linked to a different degree than the cross-linked gelatin of the main section.

In some embodiments, various methods for implanting an intraocular shunt are provided. A hollow shaft, configured to hold the intraocular shunt, can be inserted into the eye. Thereafter, the shunt can be deployed from the hollow shaft such that the shunt extends between an anterior chamber of the eye to a location of lower pressure of the eye. Once the shunt is in proper position, the hollow shaft can be withdrawn from the eye. As discussed herein, in some embodiments, the shunt can have one or more removable portions and/or one or more dissolvable sections. All or at least a portion of the shunt can be dissolvable. Further, in some embodiments, the one or more removable portions can be dissolvable.

In some embodiments, a method of treating glaucoma is provided in which an intraocular shunt is placed in an eye, in a first medical procedure. In the first procedure, the shunt can be placed to extend from an anterior chamber of the eye to a location of lower pressure of the eye. The shunt can be configured to provide a first nonzero flow rate. Thereafter, the eye can heal from the first medical procedure. Subsequent to the healing of the eye, in a second medical procedure, the intraocular shunt can be cut to provide a second flow rate, greater than the first flow rate.

The intraocular pressure of the eye can be measured in performing the method or performing checkups. After the intraocular pressure has been measured and reaches a threshold level, the step of cutting the intraocular shunt can be performed. For example, the step of cutting can be performed when the threshold level is greater than about 20 mmHg.

In some methods, in a first medical procedure as noted above, an intraocular shunt can be placed in an eye to extend from an anterior chamber of the eye to a location of lower pressure of the eye. The shunt can provide a first nonzero flow rate. However, a second medical procedure can be performed, after a threshold period of time has passed since the first medical procedure, in which the intraocular shunt is cut to provide a second flow rate, greater than the first flow rate.

For example, the step of cutting the intraocular shunt can be performed after a period of from about one week to about three months. In some cases, the step of cutting the intraocular shunt can be performed after about six (6) weeks. Further, such procedures can also be performed after permitting the eye to heal from the first medical procedure.

Methods are also provided of adjusting the flow rate of an intraocular shunt implanted in an eye. For example, a clinician can determine the position of a shunt, which has been placed in the eye to extend between an anterior chamber of the eye and a location of lower pressure of the eye. When the shunt position is determined, the clinician can thereafter cut a first portion of the shunt, thereby increasing flow through the shunt.

In some methods, prior to cutting the shunt, for example, the clinician can determine an intraocular pressure of the eye and determine a target pressure drop necessary to achieve normal intraocular pressure. Once the target pressure drop is determined, the clinician can determine a target longitudinal length of the first portion based on the target pressure drop. Accordingly, when the first portion of the shunt is cut, it can be cut at the target length.

After the first portion is cut, the first portion can be separated from the shunt. For example, the method can further comprise removing the first portion from the eye.

Additionally, the shunt can comprise a tapered lumen or tapering wall. The shunt can be cut at a specific point corresponding to a wall dimension along the taper thereof. Thus, multiple cut locations can be available in order to allow the clinician several options for target lengths or target flow rates.

The shunt can have a partially restrictive section and a main section. The partially restrictive section can have a cross-sectional area less than a cross-sectional area of the main section. The first portion can have a longitudinal length is less than a longitudinal length of the partially restrictive section.

In some embodiments, the shunt can be modified, e.g., cut, trimmed, spliced, punctured, split, etc., to adjust the flow rate of the shunt. A portion of main section can be separated from the shunt to adjust the flow. Further, when present, the partially restrictive section (in its entirety or only a fragment or section thereof) can be separated from the shunt such that flow rate of the shunt is modified, such as by increasing.

The method can comprise inserting into the eye a hollow shaft configured to hold the intraocular shunt. Thereafter, the shunt can be deployed from the hollow shaft such that the shunt forms a passage from the anterior chamber of the eye to a location of lower pressure of the eye. In some embodiments, the shunt can have a partially obstructive or flow-limiting restrictive section and an unobstructive or unrestrictive main section. The shunt can have a first flow rate or flow value with the partially restrictive section present. The method can comprise removing a portion of the partially restrictive section.

In some embodiments, a method of adjusting the flow rate of an intraocular shunt implanted in an eye can comprise determining a position of the shunt in the eye extending from (i) an anterior chamber of the eye to (ii) a location of lower pressure of the eye. The partially restrictive section can be dimensioned to have a first inner cross-sectional dimension. The main section can be dimensioned to have a second, larger inner cross-sectional dimension, different than the first dimension, through the shunt.

The first dimension can be less than the second dimension. The first and second dimensions can relate to a flow value or flow rate for the respective section. In some embodiments, the shunt or first dimension can comprise a ratio of an inner diameter to an axial length of the main section and an inner diameter to an axial length of the partially restrictive section. Further, after a fragment or section of the shunt is removed from the shunt, the shunt or second dimension can comprise a ratio of an inner diameter to an axial length of the main section and an inner diameter to an axial length of any remaining portion of the partially restrictive section. In some embodiments, a fragment or section of the partially restrictive section and/or a fragment or section of the main section can be separated from the shunt, thereby increasing the flow rate through the shunt. For example, in some embodiments, when the fragment or section of the partially restrictive section is separated from the shunt, the flow rate can increase.

The flow rate can increase from a first flow rate to a second flow rate. When the restrictive section is modified, the first flow rate is the collective flow rate through the restrictive and main sections and the second flow rate is the flow rate through the main section and any remaining portion of the restrictive section.

The shunt can be configured with various ranges of dimensions. For example, the total shunt length can be from about 4 mm to about 12 mm. In some embodiments, the total shunt length can be from about 5 mm to about 10 mm. In some embodiments, the total shunt length can be about 6 mm.

Further, the inner diameter of the main section can be from about 80 μm to about 300 μm. In some embodiments, the inner diameter of the main section can be from about 120 μm to about 200 μm. In some embodiments, the inner diameter of the main section can be about 150 μm.

The length of the partially restrictive section can be from about 0.2 mm to about 6 mm. In some embodiments, the partially restrictive section length can be from about 1 mm to about 4 mm. In some embodiments, the partially restrictive section length can be about 2 mm.

The inner diameter of the partially restrictive section can be from about 10 μm to about 70 μm. In some embodiments, the partially restrictive section inner diameter can be from about 25 μm to about 55 μm. In some embodiments, the partially restrictive section inner diameter can be about 40 μm.

The method can be performed such that separating the fragment or section of the partially restrictive section comprises removing an end portion of the shunt. The end portion of the shunt can be configured such that the wall thereof defines a smaller lumen relative to the main section. Further, separating the fragment or section of the partially restrictive section can comprise cutting the shunt using a mechanical device. Additionally, separating the fragment or section of the partially restrictive section can comprise cutting the shunt using a needle. Furthermore, separating the fragment or section of the partially restrictive section can comprise cutting the shunt using a cutting tool. For example, the cutting tool can comprise a pivot mechanism. Finally, other mechanisms or tools can be used to adjust the size or configuration of the shunt. For example, a laser can be used such that separating the fragment or section of the partially restrictive section comprises cutting the shunt using a laser.

The partially restrictive section can be positioned in a subconjunctival space. Alternatively, the partially restrictive section can be positioned in the anterior chamber of the eye.

In some embodiments, after the fragment or section of the partially restrictive section has been separated from the shunt, the method can also comprise removing the fragment or section of the partially restrictive section. However, after the fragment or section of the partially restrictive section has been separated from the shunt, the fragment or section of the partially restrictive section can be left in the eye. For example, leaving the fragment or section of the partially restrictive section in the eye can comprise leaving the fragment or section of the partially restrictive section in the subconjunctival space.

Further, the fragment or section that is separated from the shunt may be less than the entirety of the partially restrictive section. For example, separating the fragment or section of the partially restrictive section can comprise removing a first portion of the partially restrictive section from the shunt and leaving a second portion of the partially restrictive section attached to the shunt.

In some embodiments, an intraocular shunt that has an adjustable or variable flow rate can be deployed into the eye. For example, the shunt can have a partially restrictive dissolvable section and a main section. In some embodiments, the dissolvable section can define an aperture or lumen to conduct fluid therethrough. The shunt can have a first nonzero flow rate through the dissolvable section.

The method can be performed such that deploying the shunt comprises positioning the dissolvable section in the location of lower pressure. For example, the dissolvable section can be positioned in a subconjunctival space. Alternatively, however, the dissolvable section can be positioned in the anterior chamber of the eye.

The dissolvable section can comprise a dissolvable plug having a dissolution rate that is different than a dissolution rate of the main section. For example, the dissolution rate of the dissolvable plug can be a nonzero number higher than the dissolution rate of the main section, which can be zero or a nonzero number.

The dissolvable section can also comprise first and second dissolvable sections. For example, the first and second dissolvable sections can have different dissolution rates. Further, the first and second dissolvable sections can be axially spaced apart from each other. Alternatively, the first and second dissolvable sections can be concentrically layered within a lumen of the shunt.

As noted above, when a shunt having a dissolvable section is used, the method can include the steps of determining the position of the shunt in the eye extending from (i) the anterior chamber of the eye to (ii) the location of lower pressure of the eye; and separating a shunt fragment of the dissolvable section from the shunt such that the shunt has a second flow rate higher than the first flow rate.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

Figure 1:
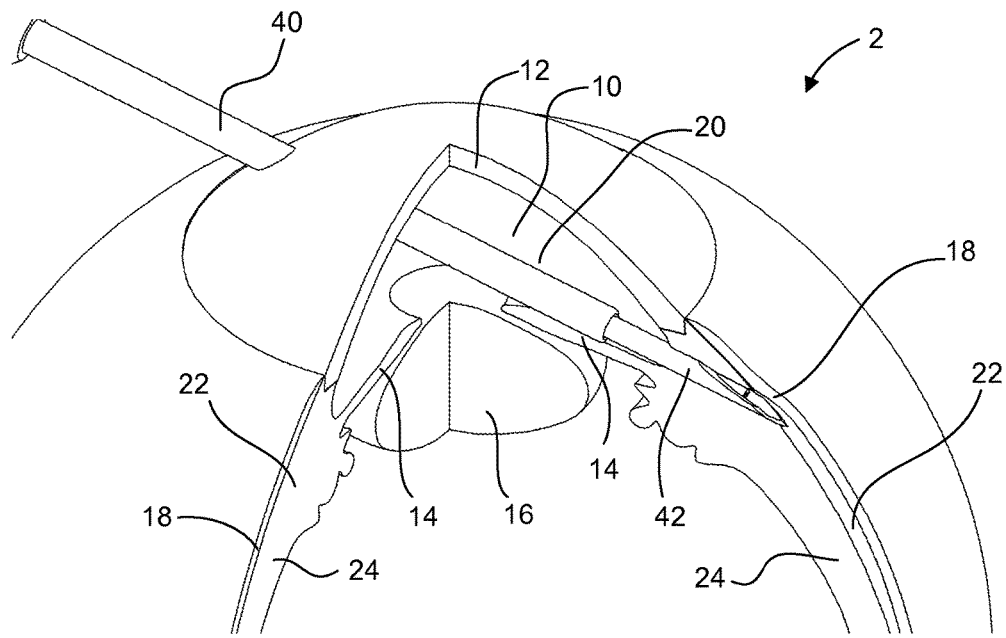
FIG. 1 is a partial cross-sectional diagram of an eye, illustrating ab interno insertion of a deployment device, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

As noted above, glaucoma filtration surgery can often result in an undesirably low intraocular pressure in the anterior chamber of the eye and can often lead to hypotony. The present disclosure provides various embodiments of methods and devices that can enable a clinician to generally prevent hypotony after a glaucoma filtration surgery while enabling the clinician to ensure adequate pressure relief by adjusting the flow through an intraocular shunt. As used herein, the term "shunt" includes hollow microfistula tubes similar to the type generally described in U.S. Pat. No. 6,544,249 as well as other structures that include one or more lumens or other flow paths therethrough.

An aspect of some embodiments is the realization that there are various unpredictable factors related to the success of a surgical intervention. Fundamentally, a successful surgical intervention relieves intraocular pressure without causing hypotony. In order to be successful, the flow through a shunt and the resulting intraocular pressure in the anterior chamber must account for various unpredictable biological factors, such as aqueous production amount, viscosity of the aqueous humor, and other biological outflow restrictions.

The biological outflow restrictions associated with a shunt depend on the overall outflow resistance or restrictions of the targeted space where the shunt is placed. The biological outflow restrictions of the subconjuctival space, for example, depend on: (1) the strength and amount and thickness of the tenon adhesions, if present (e.g., placed ab intern); (2) the thickness and consistency of conjunctiva, which can allow more or less fluid to diffuse into the sub-conjuctival vessels and into the tear film; (3) existing fibrotic adhesions; (4) the presence of lymphatic outflow pathways (some pathways may already exist at the time of shunt placement, but often the lymphatic pathways can be created and increase days and weeks after the flow has started); (5) the amount of diffusion into episcleral vessels; (6) the amount of fibrosis build-up after implant placement (which can be triggered by aqueous humor, start forming in the first one to four weeks after surgery, and can lead to a significant or total outflow restriction). Most of these factors vary greatly patient by patient and are for the most part currently unpredictable. The potential fibrotic response is the biggest changing factor in biological outflow resistance and can range from no significant outflow restriction over the first three months post-op to a total flow blockage within one week after surgery.

These patient variations and their dynamic nature post-operatively make it very difficult to maintain an optimal intraocular pressure with a "static" shunt placement. A "static" shunt placement can be referred to as a procedure or surgery in which a shunt is implanted and maintained without any change to its own flow resistance parameters or shunt outflow resistance, such as length, lumen diameter, or other features that would affect the flow rate through the shunt. Thus, excluding biological flow resistance changes in the target space, such as those mentioned immediately above, a "static" shunt or "static" shunt placement will not result in variations to the flow parameters or shunt outflow resistance of the shunt.

A static shunt usually provides substantial outflow in the early post-op phase (one day to two weeks) due to the absence of fibrotic tissue (or other biological outflow restrictions) early on. This can often lead to a less than desirable intraocular pressure in the anterior chamber for this early phase, often hypotony, and an increased risk for complications associated with such low intraocular pressures. Then, after the initial phase (e.g., after a few days to a few weeks), some patients experience a strong fibrotic response that can create high biological outflow restrictions that can result in a higher than desired intraocular pressure (e.g., above 20 mmHg).

Some embodiments disclosed herein provide a manner to overcome these complications and uncertainties of traditional surgery. For example, a flow-tunable shunt can be provided that can be modified or self-adjust after the surgery to maintain an optimal outflow resistance that can compensate for an increase in biological outflow resistance. This can allow a clinician to monitor and maintain an optimal intraocular pressure throughout changing tissue stages (e.g., changes in the biological outflow restriction of the targeted space, such as those mentioned above) that usually increase the biological outflow resistance and lead to higher intraocular pressures.

Therefore, in some embodiments, shunt devices and methods of use can provide: (1) substantial initial outflow resistance in order to avoid early low post-op intraocular pressures and hypotony; and (2) subsequent lessening of outflow resistance to compensate for a rising biological outflow resistance (e.g., fibrosis of the targeted space). The shunt can be configured such that the flow resistance is manually or surgically tuned by the clinician or specifically configured to self adjust (e.g., through the use of dissolvable sections) over time.

Methods for Shunt Placement

Various structures and/or regions of the eye having lower pressure that have been targeted for aqueous humor drainage include Schlemm's canal, the subconjunctival space, the episcleral vein, the suprachoroidal space, the intra-tenon space, and the subarachnoid space. Shunts may be implanted using an ab externo approach (e.g., entering through the conjunctiva and inwards through the sclera) or an ab interno approach (e.g., entering through the cornea, across the anterior chamber, through the trabecular meshwork and sclera). For example, ab interno approaches for implanting an intraocular shunt in the subconjunctival space are shown for example in Yu et al. (U.S. Pat. No. 6,544,249 and U.S. Patent Publication No. 2008/0108933) and Prywes (U.S. Pat. No. 6,007,511), the contents of each of which are incorporated by reference herein in its entirety.

Some methods can involve inserting into the eye a hollow shaft configured to hold an intraocular shunt. In certain embodiments, the hollow shaft can be a component of a deployment device that may deploy the intraocular shunt. The hollow shaft can be coupled to a deployment device or be part of the deployment device itself. Deployment devices that are suitable for deploying shunts according to the invention include, but are not limited to the deployment devices described in U.S. Pat. No. 6,007,511, U.S. Pat. No. 6,544,249, and U.S. Publication No. US2008/0108933, the contents of each of which are incorporated herein by reference in their entireties. The deployment devices can include devices such as those as described in co-pending and co-owned U.S. patent application Ser. No. 12/946,222, filed on Nov. 15, 2010, U.S. patent application Ser. No. 12/946,645, filed on Nov. 15, 2010, and co-pending U.S. application Ser. No. 13/314,939, filed on Dec. 8, 2011 (AQUE-015/00US), the contents of each of which are incorporated by reference herein in their entireties.

The shunt can be deployed from the shaft into the eye such that the shunt forms a passage from the anterior chamber into an area of lower pressure, such as Schlemm's canal, the subconjunctival space, the episcleral vein, the suprachoroidal space, the intra-tenon space, the subarachnoid space, or other areas of the eye. The hollow shaft is then withdrawn from the eye. Methods for delivering and implanting bioabsorbable or permanent tubes or shunts, as well as implantation devices for performing such methods, are generally disclosed in applicant's co-pending applications, U.S. application Ser. No. 13/314,939, filed on Dec. 8, 2011 (AQUE-015/00US), and U.S. Application No. US2012/0197175, filed on Dec. 8, 2011 (AQUES-009/06US), as well as in U.S. Pat. Nos. 6,544,249 and 6,007,511, each of which are incorporated by reference in their entireties. Embodiments of the shunts disclosed herein can be implanted using such methods and others as discussed herein.

Some methods can be conducted by making an incision in the eye prior to insertion of the deployment device. However, in some instances, the method may be conducted without making an incision in the eye prior to insertion of the deployment device. In certain embodiments, the shaft that is connected to the deployment device has a sharpened point or tip. In certain embodiments, the hollow shaft is a needle. Exemplary needles that may be used are commercially available from Terumo Medical Corp. (Elkington, Md.). In some embodiments, the needle can have a hollow interior and a beveled tip, and the intraocular shunt can be held within the hollow interior of the needle. In some embodiments, the needle can have a hollow interior and a triple ground point or tip.

Some methods can be conducted without needing to remove an anatomical portion or feature of the eye, including but not limited to the trabecular meshwork, the iris, the cornea, or aqueous humor. Some methods can be conducted without inducing substantial ocular inflammation, such as subconjunctival blebbing or endophthalmitis. Some methods can be achieved using an ab interno approach by inserting the hollow shaft configured to hold the intraocular shunt through the cornea, across the anterior chamber, through the trabecular meshwork, and into the intra-scleral or intra-tenon space. However, some methods may be conducted using an ab externo approach.

In some methods conducted using an ab interno approach, the angle of entry through the cornea can be altered to affect optimal placement of the shunt in the intra-tenon space. The hollow shaft can be inserted into the eye at an angle above or below the corneal limbus, in contrast with entering through the corneal limbus. For example, the hollow shaft can be inserted from about 0.25 mm to about 3.0 mm above the corneal limbus. The shaft can be inserted from about 0.5 mm to about 2.5 mm above the corneal limbus. The shaft can also be inserted from about 1.0 mm to about 2.0 mm above the corneal limbus, or any specific value within any of these ranges. For example, the hollow shaft can be inserted above the corneal limbus at distances of about: 1.0 mm, 1.1 mm, 1.2 mm, 1.3 mm, 1.4 mm, 1.5 mm, 1.6 mm, 1.7 mm, 1.8 mm, 1.9 mm, or 2.0 mm.

Further, in some embodiments, placement of the shunt farther from the limbus at the exit site, as provided by an angle of entry above the limbus, can provide access to more lymphatic channels for drainage of aqueous humor, such as the episcleral lymphatic network, in addition to the conjunctival lymphatic system. A higher angle of entry also results in flatter placement in the intra-tenon space so that there is less bending of the shunt.

As discussed in Applicant's co-pending application, U.S. application Ser. No. 13/314,939, filed on Dec. 8, 2011 (AQUE-015/00US), the entirety of which is incorporated herein by reference, in certain embodiments, to ensure proper positioning and functioning of the intraocular shunt, the depth of penetration into the intra-tenon space may be important when performing some methods.

In some methods, the distal tip of the hollow shaft can pierce the sclera and intra-tenon space without coring, removing or causing major tissue distortion of the surrounding eye tissue. The shunt is then deployed from the shaft. Preferably, a distal portion of the hollow shaft (as opposed to the distal tip) completely enters the intra-tenon space before the shunt is deployed from the hollow shaft.

In accordance with some embodiments, the hollow shaft can comprise a flat bevel needle, such as a needle having a triple-ground point. The tip bevel can first pierce through the sclera and into the intra-tenon space by making a horizontal slit. In some methods, the needle can be advanced even further such that the entire flat bevel penetrates into the intra-tenon space, to spread and open the tissue to a full circular diameter.

Further, in accordance with an aspect of some methods, the intra-tenon channel can be urged open by the flat bevel portion of the needle so that the material around the opening is sufficiently stretched and a pinching of the shunt in that zone is avoided, thus preventing the shunt from failing due to the pinching or constriction. Full entry of the flat bevel into the intra-tenon space causes minor distortion and trauma to the local area. However, this area ultimately surrounds and conforms to the shunt once the shunt is deployed in the eye.

With reference to the figures, FIG. 1 is a schematic diagram that illustrates a manner of accessing the eye and delivering an intraocular shunt for treatment of glaucoma. As noted, some methods disclosed herein provide for an ab interno approach. As also noted, the ab interno approach may not be needed in order to perform the procedures or methods disclosed herein. For example, the shunt can be delivered using an ab externo approach, as discussed herein.

FIG. 1 illustrates the general anatomy of an eye 2. As illustrated, an anterior aspect of the anterior chamber 10 of the eye 2 is the cornea 12, and a posterior aspect of the anterior chamber 10 of the eye 2 is the iris 14. Beneath the iris 14 is the lens 16. The conjunctiva 18 is a thin transparent tissue that covers an outer surface of the eye 2. The anterior chamber 10 is filled with aqueous humor 20. The aqueous humor 20 drains into a space(s) 22 below the conjunctiva 18 through the trabecular meshwork (not shown in detail) of the sclera 24. The aqueous humor 20 is drained from the space(s) 22 below the conjunctiva 18 through a venous drainage system (not shown).

FIG. 1 illustrates a surgical intervention to implant an intraocular shunt into the eye using a delivery device 40 that holds the shunt, and deploying the shunt within the eye 2. FIG. 1 illustrates an ab interno approach in which the delivery device 40 has been inserted through the cornea 12 into the anterior chamber 10. As noted above, however, the implant can also be placed using an ab externo approach, in which the conjunctiva or tenons can be dissected and pulled back, prior to placement of a shunt.

Referring to FIG. 1, the delivery device 40 can be advanced across the anterior chamber 10 in what is referred to as a transpupil implant insertion. The delivery device can be inserted through the anterior angle and advanced through the sclera 24 until accessing a targeted space, such as Schlemm's canal, the subconjunctival space, the episcleral vein, an episcleral bleb, the suprachoroidal space, the intra-tenon space, the sub-tenon's space, the subarachnoid space, a created intrascleral space, or other areas, as desired. The shunt is then deployed from the deployment device, producing a conduit between the anterior chamber and the targeted space to allow aqueous humor to drain through the traditional drainage channels of the eye, such as the intra-scleral vein, the collector channel, Schlemm's canal, the trabecular outflow, the uveoscleral outflow to the ciliary muscle, the conjunctival lymphatic system, or others.

In some embodiments, the delivery device 40 can comprise a hollow shaft 42 that is configured to hold an intraocular shunt. The shaft may hold the shunt within the hollow interior of the shaft. Alternatively, the hollow shaft may hold the shunt on an outer surface of the shaft.

Figure 2:
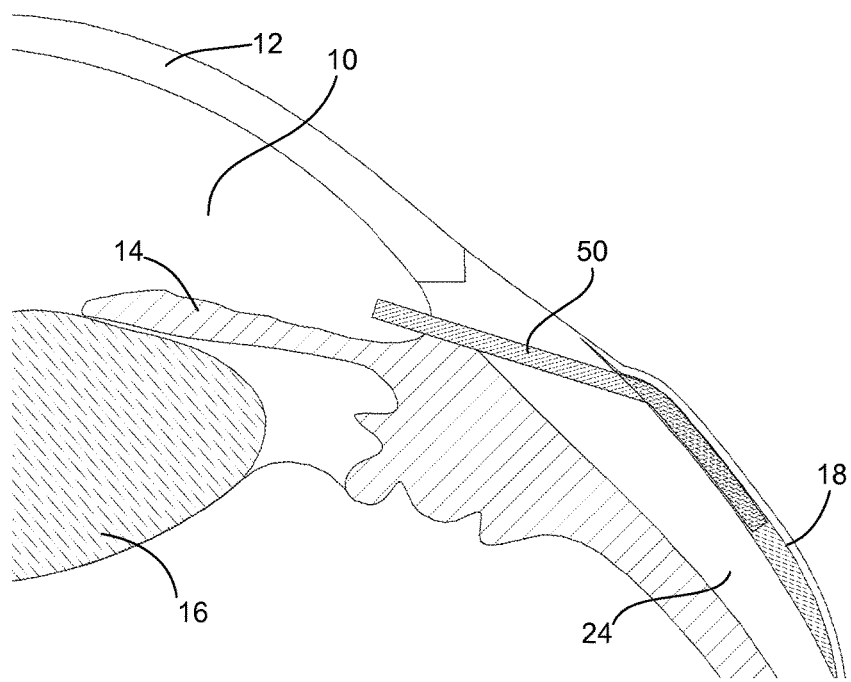
FIG. 2 illustrates a schematic placement of an intraocular shunt within intra-tenon space, according to some embodiments.

FIG. 2 provides a cross-sectional view of a portion of the eye 2, and provides greater detail regarding certain anatomical structures of the eye and placement of an intraocular shunt 50. In particular, FIG. 2 shows the shunt 50 implanted in the intra-tenon space between the conjunctiva 18 and the sclera 24. In some embodiments, intra-tenon placement can be achieved by not dissecting the conjunctiva, by controlling the scleral exit location, and by pre-treatment of the intra-tenon space before or by tenon manipulation during the procedure. Placement of shunt 50 within the intra-tenon space allows aqueous humor 20 to diffuse into the subconjunctival space. According to some embodiments, the outflow restrictions of the subconjunctival space can depend on the strength, amount, and thickness of the tenon adhesions (if present, e.g., when placed ab interno), the thickness and consistency of the conjunctiva (which can allow more or less fluid to diffuse into the subconjunctival vessels and tear space), and existing fibrotic adhesions.

FIG. 2 illustrates one of a variety of potential placements of the shunt 50 in the eye. As discussed herein, methods and devices provided herein can be implemented wherein a shunt is placed in communication with other anatomical features of the eye. Thus, some methods and devices disclosed herein can be implemented when a shunt forms a passage from the anterior chamber into an area of lower pressure, such as Schlemm's canal, the subconjunctival space, the episcleral vein, the suprachoroidal space, the intra-tenon space, the subarachnoid space, or other areas of the eye.

The methods of implantation may be fully automated, partially automated (and, thus, partially manual), or completely manual. For example, in a fully automated procedure, a shunt may be delivered by robotic implantation whereby a surgeon controls the advancement of the needle, plunger, optional guidewire and, as a result, shunt by remotely controlling a robot. In such fully automated, remotely controlled procedures, the surgeon's hands typically do not contact implantation apparatus during the surgical procedure. Alternatively, shunt may be delivered to the desired area of the eye with a "handheld" implantation apparatus. Handheld implantation devices, as well as details regarding steps and procedures of implantation methods, are described in co-pending U.S. Application Publication No. 2012/0197175, filed on Dec. 8, 2011 (AQUE-009/06US) and Ser. No. 13/314,939, filed on Dec. 8, 2011 (AQUE-015/00US), the entireties of each of which are incorporated herein by reference. Insertion of the needle into the eye as well as certain repositioning or adjusting steps may be performed manually by the surgeon. In the case of fully manual devices and methods, all of the positioning, repositioning, adjusting and implantation steps can be performed manually by the surgeon.

Intraocular Shunt Devices

Some embodiments disclosed herein comprise intraocular shunts that are configured to form a drainage pathway from the anterior chamber of the eye to a targeted space. In this manner, the shunt can allow aqueous humor to drain from the anterior chamber and out through the traditional drainage channels of the eye, such as the intra-scleral vein, the collector channel, Schlemm's canal, the trabecular outflow, the uveoscleral outflow to the ciliary muscle, the conjunctival lymphatic system, or others.

Some embodiments disclosed herein comprise a shunt that is generally cylindrically shaped with an outside cylindrical wall and, in some embodiments, a hollow interior that extends at least partially along the length of the shunt. The shunt can have an inner wall defining a main section inner diameter, lumen dimension, diameter or a flow path cross-sectional dimension or diameter of from about 10 μm to about 300 μm. The shunt can have an inner wall defining a lumen dimension or diameter of from about 50 μm to about 250 μm. Further, the shunt can have an inner wall defining a lumen dimension or diameter of from about 100 μm to about 200 μm. In some embodiments, the shunt can have an inner wall defining a lumen dimension or diameter of about 150 μm.

The inner diameter of the partially restrictive section can be from about 10 μm to about 70 μm. In some embodiments, the partially restrictive section inner diameter can be from about 25 μm to about 55 μm. In some embodiments, the partially restrictive section inner diameter can be about 40 μm.

The outside dimension or diameter of the wall of some embodiments can be from about 190 to about 300 μm. Further, the wall thickness of some embodiments can be from about 30 μm to about 70 μm.

In some embodiments, the intraocular shunt can have a length that is sufficient to form a drainage pathway from the anterior chamber of the eye to the targeted space. The length of the shunt is important for achieving placement specifically in the targeted space. A shunt that is too long will extend beyond the targeted space and may irritate the eye. For example, if the targeted space is the intra-scleral space, a shunt that is too long can irritate the conjunctiva which can cause the filtration procedure to fail. Further, in such embodiments, a shunt that is too short will not provide sufficient access to drainage pathways such as the episcleral lymphatic system or the conjunctival lymphatic system.

In some embodiments, the shunt may be any length that allows for drainage of aqueous humor from an anterior chamber of an eye to the targeted space. In some embodiments, the shunt can have a total length in the range of from about 1 mm to about 12 mm. The length can also be in the range of from about 2 mm to about 10 mm or from about 4 mm to about 8 mm, or any specific value within said ranges. In some embodiments, the length of the shunt is from about 6 mm to about 8 mm, or any specific value within this range, for example, such as about: 6.0 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm. 7.9 mm, or 8.0 mm.

Of the total shunt length, the length of the partially restrictive section can be from about 0.2 mm to about 6 mm. In some embodiments, the partially restrictive section length can be from about 1 mm to about 4 mm. In some embodiments, the partially restrictive section length can be about 2 mm.

Additionally, some embodiments of the shunt can have different shapes and different dimensions that may be accommodated by the eye. In accordance with embodiments disclosed herein, the intraocular shunt can be formed having dimensions within the various ranges of dimensions disclosed for outer diameter (e.g., of the main section or partially restrictive section), inner diameter (e.g., of the main section or partially restrictive section), segment lengths (e.g., of the partially restrictive section or main section), and total length.

For example, some embodiments can be configured such that the shunt has a total length of about 6 mm, a main section inner diameter of about 150 μm, and a partially restrictive section inner diameter of from about 40 μm to about 63 μm.

Surgeon-Controlled Flow-Tunable Shunts

The figures illustrate embodiments of an intraocular implant or shunt that can have a first flow that can be modified to a second flow by changing the configuration of the implant.

Some implants can be configured to have a first flow that can be changed to a second flow by shortening the length of the implant. Some implants can be configured to have a first flow that can be changed to a second flow by removing a restrictive section thereof. In some embodiments, the first flow can be less than the second flow through the implant. Thus, modification, shortening, or removal of a section thereof can increase the flow through the implant.

For example, the figures illustrate embodiments and configurations of flow-tunable implants or shunts having one or more partially obstructive or flow-limiting restrictive sections and one or more unobstructive or unrestrictive main sections.

Embodiments of the shunts disclosed herein can provide a desired initial flow resistance or flow value that prevents excessive outflow from the anterior chamber of the eye, thus avoiding low intraocular pressures or hypotony. However, upon development of biological outflow resistance, a clinician can tune the flow resistance or flow value of the shunt to prevent high intraocular pressure. Accordingly, embodiments herein enable a clinician to adjust or tune the flow rate of the shunt. The geometric configuration and dimensions of components of these shunts can be manipulated as desired to provide a desired flow resistance. Accordingly, the embodiments illustrated and discussed do not limit the scope of the features or teachings herein.

In accordance with some embodiments, the shunt can be configured such that the clinician can adjust the flow resistance or flow value to provide a flow rate of from about 1 μm per minute to about 3 μm per minute. Further, the shunt can be configured such that the clinician can adjust the flow resistance or flow value to provide a flow rate of about 2 μm per minute.

Figure 3:
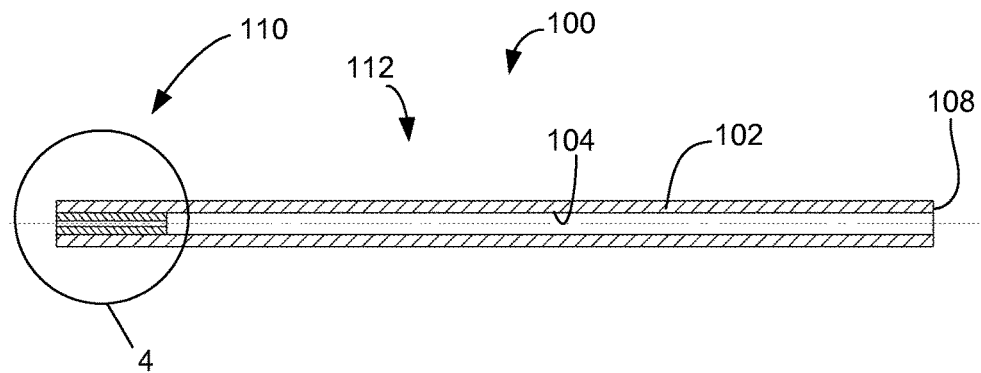
FIG. 3 illustrates a cross-sectional view of an intraocular shunt, according to some embodiments.

FIG. 3 illustrates a shunt 100 having an elongate body having an inner wall 102 that defines a shunt lumen 104 extending therethrough. The shunt 100 can comprise opposing ends 106, 108 (inlet/outlet). The end 106 can be a restrictive end, and the end 108 can be a clear end. The shunt 100 can comprise a partially obstructive or flow-limiting restrictive section 110 and a unobstructive or unrestrictive main section 112. Flow can be provided through the partially restrictive section 110, but with greater resistance than through the main section 112. The shunt lumen 104 can extend through the main section 112. The partially restrictive section 110 can comprise a gelatin tube. The gelatin tube can be inserted into the shunt lumen 104. The a partially restrictive section 110 or gelatin tube can comprise a wall 118 that defines a secondary lumen 120. The wall 118 can define a different inner dimension than the wall 102. For example, the wall 118 can define a cross-section or profile that is smaller than the cross-section or profile of the wall 102, thus rendering the lumen 104 larger than the lumen 120. In some embodiments, the secondary lumen 120 can extend generally coaxially with the shunt lumen 104; however, the secondary lumen 120 can be configured to be spaced apart from a central axis of the shunt lumen 104.

For example, the secondary lumen 120 can also extend longitudinally along the partially restrictive section 110 while traversing and/or being spaced apart from the central axis of the partially restrictive section 110. Thus, the wall 118 can define a variable thickness. Further, the secondary lumen 120 can be encircled by the wall 118 forming the partially restrictive section 110. However, the wall 118 can be discontinuous, and the secondary lumen 120 can be bounded intermediate the wall 118 of the partially restrictive section 110 and the wall 102. Thus, the lumen 104 and the lumen 120 can have a boundary surface in common, in some embodiments.

Further, the partially restrictive section 110 can be attached to the shunt 100 either permanently or removably. For example, the partially restrictive section 110 can be a separate peace that is permanently attached to the shunt 100 or formed with the shunt 100 as a single piece. However, the partially restrictive section 110 can also be removably attached to the shunt 100, thereby allowing the partially restrictive section 110 to be completely or at least partially removed from the shunt 100. For example, the partially restrictive section 110 can be a metal stylus or structure that is inserted into the shunt lumen 104, which can later be removed.

The shunt 100 can be configured such that two or more sections thereof comprise different flow restrictions or flow values. Thus, in some instances, a clinician can manually manipulate or adjust the overall flow restriction or flow value of the shunt 100 by manipulating one or more sections of the shunt 100. Further, in some instances, a clinician can utilize a shunt or shunt system that self-adjusts or passively adjusts to change the overall flow restriction or flow value of the shunt over time.

The flow resistance or flow value of a given section of the shunt can relate to the geometric constraints or properties of the given section. The geometric constraints or properties can be one or more of the diameter or radius, the length of the given section, a cross-sectional area of the flow passage, surface roughness, or other such geometrics characteristics. In some embodiments, for purposes of this disclosure, the flow resistance or flow value can be a numeric representation, coefficient, or formula upon which the mathematical calculation for a fluid flow rate through the given section for a given fluid is predicated. For example, the flow value can represent a ratio of an inner diameter or radius to an axial length of the given section. A higher flow value could result in a higher flow rate. Further, in some embodiments, the flow resistance can be the inverse of the flow value, e.g., a ratio of an axial length to an inner diameter or radius of the given section. Generally, a higher flow resistance would result in a lower flow rate. Further, the flow resistance can depend mainly on the shunt length, inner diameter and viscosity of the liquid (Aqueous Humor).

The flow through the shunt, and thus the pressure exerted by the fluid on the shunt, is calculated by the Hagen-Poiseuille equation:

$$\Phi = \frac{dV}{dt} = v\pi R^2 = \frac{\pi R^4}{8\eta}\left(\frac{-\Delta P}{\Delta x}\right) = \frac{\pi R^4}{8\eta}\frac{|\Delta P|}{L}$$

where $\Phi$ is the volumetric flow rate; V is a volume of the liquid poured (cubic meters); t is the time (seconds); v is mean fluid velocity along the length of the tube (meters/second); $\Delta x$ is a distance in direction of flow (meters); R is the internal radius of the tube (meters); $\Delta P$ is the pressure difference between the two ends (pascals); $\eta$ is the dynamic fluid viscosity (pascalsecond (Pa·s)); and L is the total length of the tube in the x direction (meters).

For example, the shunt 100 can be configured such that the flow through the partially restrictive section 110 defines a first flow resistance or flow value. The main section 112 can define a first flow cross-sectional area, and the partially restrictive section 110 can define a second flow cross-sectional area that is less than the first flow cross-sectional area. The first flow resistance or flow value can be determined by geometric constraints or properties of the partially restrictive section 110. Such constraints can include the length of the partially restrictive section 110, the inner diameter or radius of the wall 118, and other features, such as an inner surface roughness of the wall 118.

Further, the second flow cross-sectional area or profile of the partially restrictive section 110 can be any of a variety of geometric profiles. For example, the second flow cross-sectional area or profile can be circular, rectangular, square, polygonal, or otherwise shaped. The second flow cross-sectional area or profile can be configured to provide less cross-sectional area than the main section 112. The second flow cross-sectional area or profile can be constant or variable along the longitudinal extent of the partially restrictive section 110.

Similarly, the main section 112 can define a flow resistance or flow value that is different than the first flow resistance or flow value of the partially restrictive section 110. As with the first flow resistance or flow value, the flow resistance or flow value of the main section 112 can be determined by geometric constraints or properties of the main section 112, as discussed above. Accordingly, the geometric constraints of the main section 112 can differ from the geometric constraints of the partially restrictive section 110, resulting in different flow resistances or flow values.

The total pressure drop across the shunt $\Delta P_{total}$ consisting of a main section and a partially constrained section can be calculated for each section separately as $\Delta P_{main}$ and $\Delta P_{partially\ constrained}$, according to the formula above:

$$\Delta P = \frac{8\Phi\eta L}{\pi R^4}$$

and then by adding the two numbers together: $\Delta P_{total} = \Delta P_{main} + \Delta P_{partially\ constrained}$. If there are more than 2 sections, then they are added together accordingly.

$\Delta P_{total}$ for any given shunt represents the minimum IOP in the eye for any given flow rate $\Phi$. The flow rate $\Phi$ through the shunt is depending on the shunt location and amount of surrounding tissue resistance normally from about 10% to about 90% of the amount of aqueous production in the eye which is typically from about 1 to about 3 µl/min.

Figure 4:
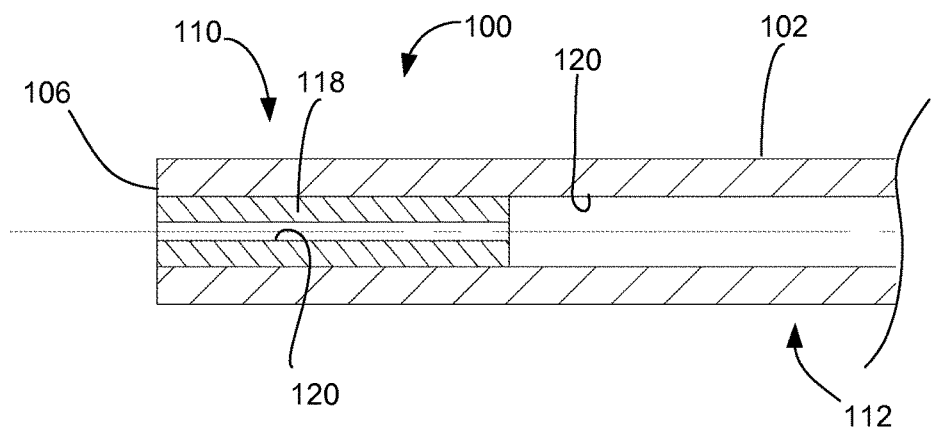
FIGS. 4-7 illustrate cross-sectional views of an end of an intraocular shunt of FIG. 3, according to some embodiments.

As illustrated in FIGS. 3-4, the shunt wall 102 can be configured such that the lumen 104 is large for most of the shunt length, which would provide very little flow resistance. However, the inner dimension of the wall 118 of the partially restrictive section 110 can be much smaller than the inner dimension of the wall 102, which can constrain flow through the shunt 100 to the first flow resistance or flow value.

As illustrated in FIGS. 3-4, the shunt 100 can comprise a single partially restrictive section 110 and a single main section 112. However, the shunt 100 can comprise multiple partially restrictive sections and multiple main sections (see related embodiments shown in FIGS. 18-19).

A given partially restrictive section can also define a plurality of cross-sectional flow areas or inner diameters. For example, as illustrated in FIG. 5, the partially restrictive section can have distinct steps or subsections that have distinct cross-sectional flow areas or inner diameters.

Figure 5:
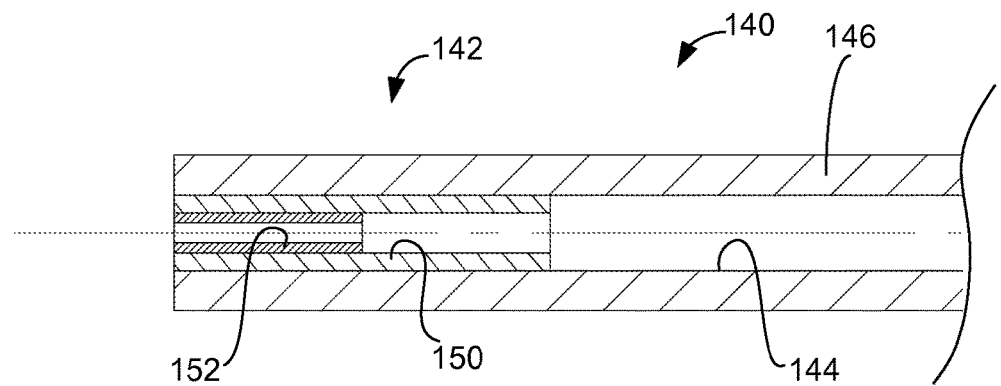

FIG. 5 illustrates an embodiment of a shunt 140 in which a partially obstructive or flow-limiting restrictive section 142 comprises first and second occluding components 150, 152. The first occluding component 150 and the second occluding component 152 can be inserted into a lumen 144, formed by a shunt wall 146 of the shunt 140. The first and second occluding component 150, 152 can also be pre-assembled prior to insertion into the shunt lumen 144. The first and second occluding components 150, 152 can define different inner cross-sectional dimensions (e.g., diameters) that provide distinct flow resistances or flow values. Accordingly, in some embodiments, a clinician can adjust or configure more than two flow resistances or flow values to manipulate the overall flow resistance or flow value of the shunt.

In some embodiments, the partially restrictive section can be formed using a material or component that is formed separately from the restrictive end and later joined thereto.

For example, similar to the embodiment illustrated in FIG. 5, the partially restrictive section can be formed using a tube configured to fit within the shunt lumen. Further, the partially restrictive section can be formed using a component, coating, or other material that is layered along the inner surface of the shunt wall. The component, coating, or other material can extend at least partially about the circumference of the inner surface of the shunt wall. In some embodiments, the component, coating, or other material can extend fully about the circumference, and in some embodiments, the component, coating, or other material can extend longitudinally along the inner surface of the shunt wall. In any configuration, the overall cross-sectional flow area of the partially restrictive section can be less than the overall cross-sectional flow area of the main section.

In some embodiments, a partially restrictive section can be formed by varying a dimension of the shunt along that partially restrictive section. Thus, the partially restrictive section can be formed integrally or of a single, continuous piece of material with the shunt.

Figure 6:
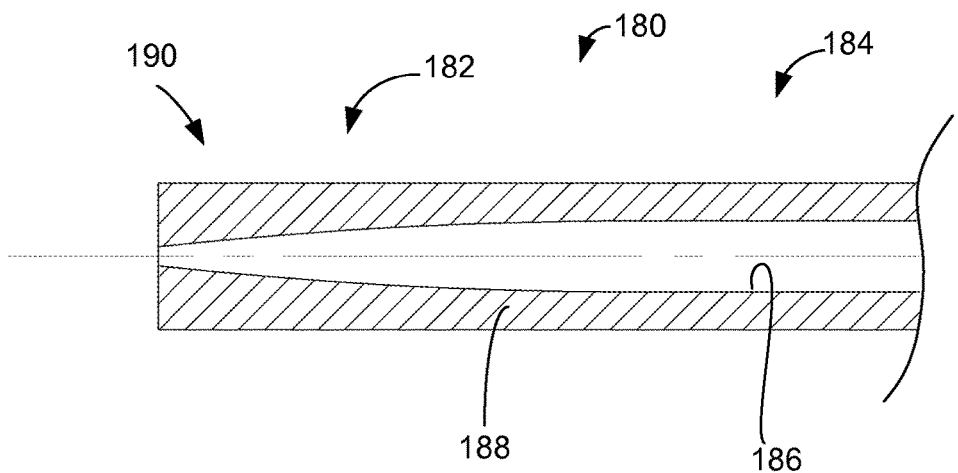

For example, as illustrated in FIG. 6, another embodiment of a shunt 180 is illustrated in which a partially obstructive or flow-limiting restrictive section 182 is formed integrally or as a single, continuous piece with a main section 184 of the shunt 180. In these embodiments, a lumen 186 defined by a wall 188 of the shunt 180 tapers towards a restrictive end 190 thereof as the thickness of the wall 188 increases. The tapering can be linear or nonlinear. In either configuration, the tapering of the shunt lumen 186 will tend to create a change in the flow resistance or flow value between the main section 184 and the partially restrictive section 182. Additionally, the tapering can be stepwise, as similarly shown in the embodiment of FIG. 5.

Figure 7:
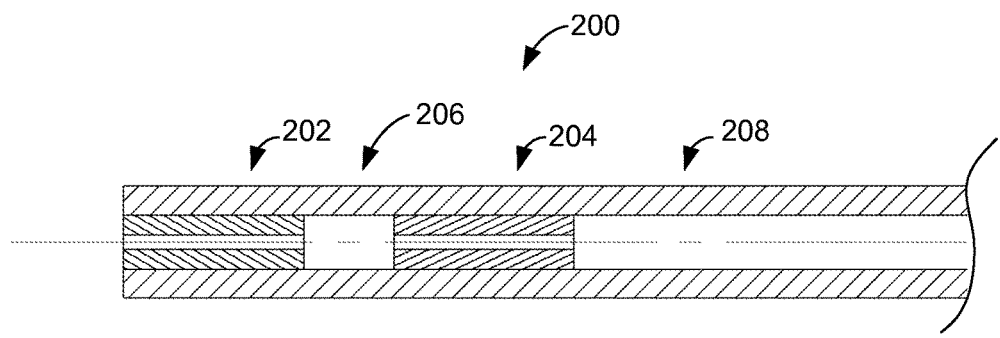

FIG. 7 illustrates yet another embodiment of a shunt 200 having a plurality of partially obstructive or flow-limiting restrictive sections 202, 204 and a plurality of main sections 206, 208. The partially restrictive sections 202, 204 can comprise identical or different flow resistances or flow values. As illustrated, the partially restrictive section 202 can define a slightly longer axial length than the partially restrictive section 204. Accordingly, the flow resistance for the partially restrictive section 202 can be greater than the flow resistance for the partially restrictive section 204. In some embodiments, the inner diameter or radius of the partially restrictive sections 202, 204 can also vary. Further, the main section 206 can be disposed between the partially restrictive sections 202, 204.

As with any of the geometric parameters of embodiments taught or disclosed herein, the distance between the partially obstructive or flow-limiting restrictive sections 202, 204 can be varied in order to achieve a desired overall flow resistance or flow value for the shunt.

Methods for Adjusting Shunt Flow Resistance

Using a flow-tunable shunt disclosed and taught herein, a clinician can modify the flow resistance or flow value of one or more portions of the shunt to adjust the overall flow resistance or flow value of the shunt. This allows the clinician to ensure that the shunt maintains an optimal overall flow resistance in response to any increase in biological outflow resistance. Thus, during postoperative visits, the clinician can monitor any changes in the tissue surrounding the shunt or the drainage channels, measure and track the intraocular pressure, and when necessary, adjust or modify the flow resistance or flow value in order to maintain an optimal intraocular pressure.

As noted above, after a shunt is placed in the eye has healed, the surrounding tissue can create biological outflow resistance, such as fibrosis, which can limit or reduce the flow through the shunt. The tissue reaction that changes the overall outflow resistance of the shunt typically stabilizes after about 1-10 weeks after the surgery.

A clinician can conduct a post-operative checkup to modify the shunt in a subsequent procedure after a threshold period of time has passed. This period of time can be from about eight weeks to about three months. Often, ten weeks can be a sufficient amount of time in order to achieve stabilization and healing. If appropriate, the modification of the shunt can be performed as a matter of course.

As part of the post-operative checkup, the clinician can verify whether the intraocular pressure is at a desired level. Generally, normal intraocular pressure is from about 10 mmHg and about 20 mmHg. Should the intraocular pressure be at an undesirable level (e.g., greater than 20 mmHg), the clinician can modify the shunt accordingly.

The clinician can modify the shunt to reduce the flow resistance or flow value of the shunt. For example, the clinician can cut the shunt, and in some cases, remove a portion thereof from the eye. The cutting of the shunt can increase the flow through the shunt, thereby relieving and reducing the intraocular pressure.

Accordingly, in some embodiments, methods and devices are provided by which a shunt can provide: (1) substantial initial outflow resistance in order to avoid early low post-op intraocular pressures and hypotony, and (2) the ability to subsequent reduce outflow resistance to compensate for a rising biological outflow resistance (e.g., fibrosis of the targeted space).

Mechanical Modification of the Shunt

In order to change the flow resistance or flow value of the shunt, some embodiments of the shunt can be configured such that the clinician can splice, cut, puncture, or otherwise remove one or more aspects, fragments, or sections or all of the partially obstructive or flow-limiting restrictive section (s) of the shunt. In some instances, the clinician can cut off a portion of the restrictive end of the shunt and thereby open up the flow for an optimal long-term intraocular pressure performance.

In some methods, the shunt can be positioned such that a restrictive end is disposed in the anterior chamber of the eye. Further, in some methods, the shunt can be positioned such that a restrictive end is disposed in the targeted space or a location of lower pressure. Furthermore, in some embodiments, the shunt can be configured and positioned such that one or more partially obstructive or flow-limiting restrictive sections or ends are situated in the anterior chamber and the targeted space.

Figure 8:
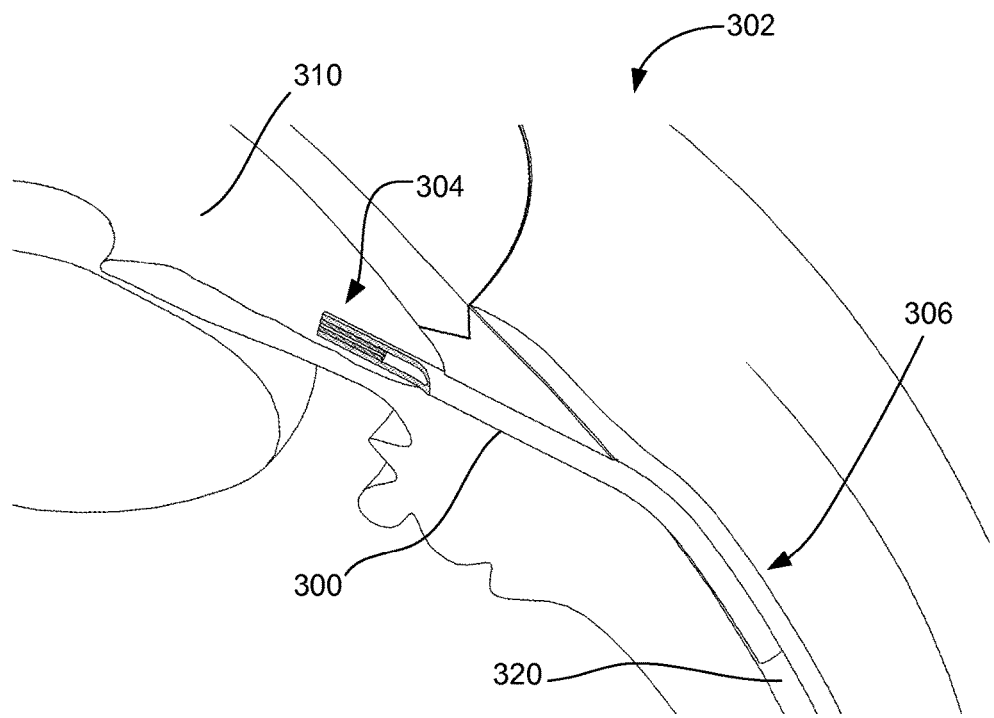
FIG. 8 illustrates placement of an intraocular shunt with a partial cross-sectional view of a partially restrictive section disposed in an anterior chamber of the eye, according to some embodiments.

For example, FIG. 8 illustrates a shunt 300 that is implanted into an eye 302. The shunt 300 can comprise a restrictive end 304 and a clear end 306. The restrictive end 304 can be positioned in the anterior chamber 310 of the eye 302. Further, the clear end 306 can be placed in a subconjunctival space 320 of the eye 302. Thus, the shunt 300 can be operative to provide pressure relief of the fluid in the anterior chamber 310 to a location of lower pressure, the subconjunctival space 320 of the eye 302. As noted above, while the restrictive end 304 can tend to ensure that the condition of low intraocular pressure is avoided, such as hypotony, over time, certain biological outflow restrictions can be formed, which can reduce the overall outflow or flow rate of the shunt 300. Accordingly, a clinician can modify the shunt 300 in order to change the flow resistance or flow value of the shunt 300 to compensate for later-developing biological outflow restrictions.

Figure 9:
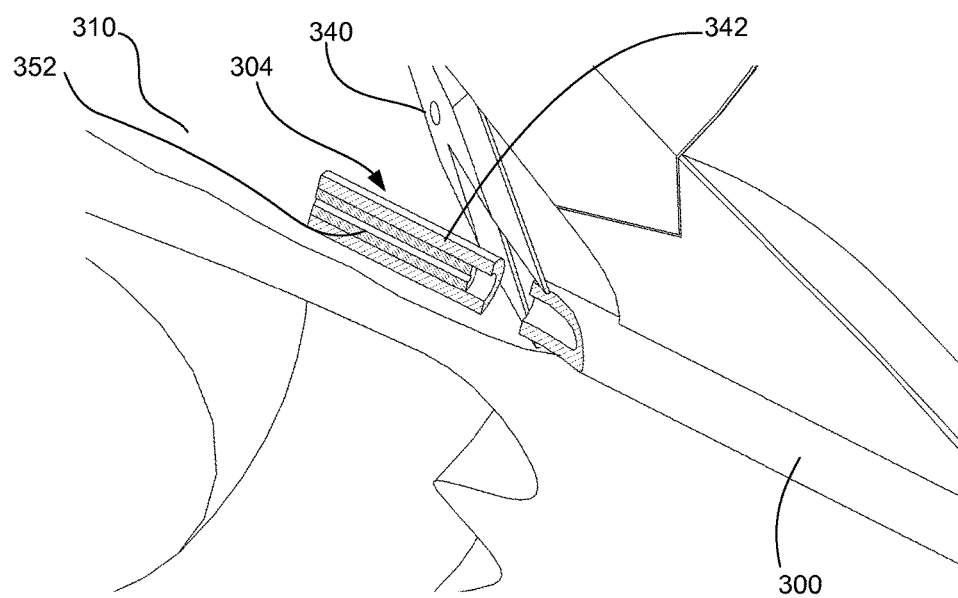
FIG. 9 illustrates the severance of a portion of the partially restrictive section of the shunt illustrated in FIG. 8, according to some embodiments.
Figure 10:
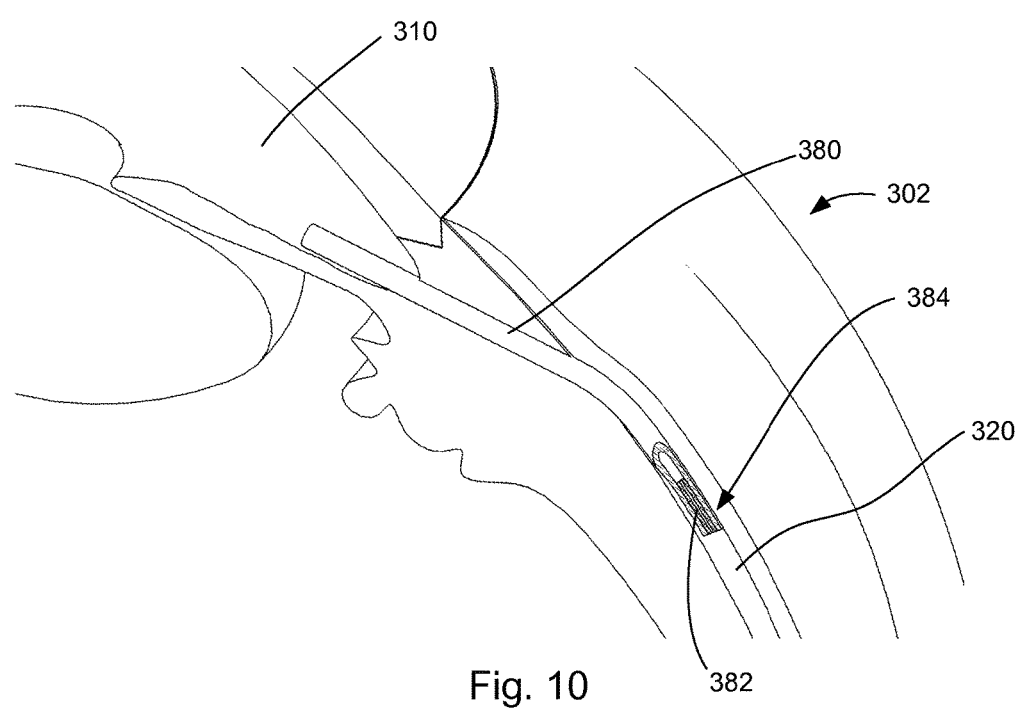
FIG. 10 illustrates placement of an intraocular shunt wherein a partially restrictive section is disposed in subconjunctival space, according to some embodiments.
Figure 11:
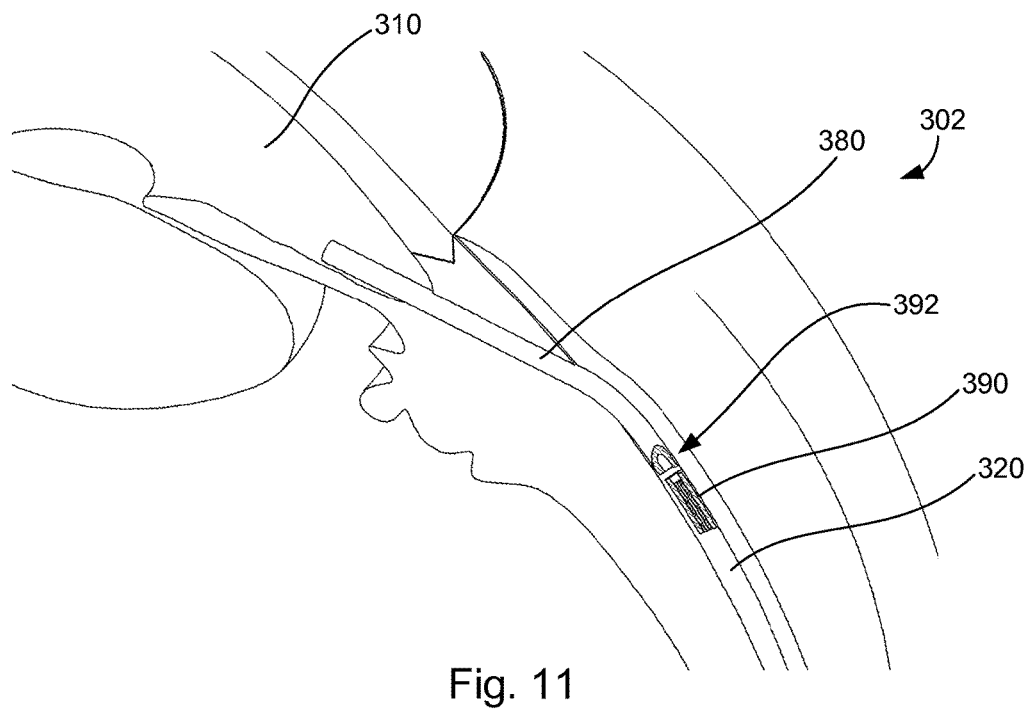
FIG. 11 illustrates the severance of a portion of the partially restrictive section of a shunt, oriented as illustrated in FIG. 10, according to some embodiments.

FIG. 9-11 illustrate different aspects of embodiments in which the shunt can be mechanically modified. For example, FIG. 9 illustrates an embodiment of a method for mechanically modifying the shunt 300 in order to adjust the flow resistance or flow value of the shunt 300. As illustrated, a mechanical cutting device 340 can be moved into the anterior chamber 310 of the eye 302. The cutting device 340 can comprise one or more sharpened portions configured to engage or cut the shunt 300. For example, the cutting device 340 can comprise a needle having a sharpened end, scissors, or other micro devices suitable for use in the eye 302.

Once the cutting device 340 is moved into the anterior chamber 310, a portion 342 of the restrictive end 304 can be removed from the shunt 300. The portion 342 can be all or part of a partially obstructive or flow-limiting restrictive section 352 of the shunt 300. As illustrated, in some embodiments, the portion 342 can be an entirety of the partially restrictive section 352 of the shunt 300, which can be removed from the shunt 300 by cutting the shunt 300 at a location distal to the partially restrictive section 352 of the restrictive end 304. Thereafter, in embodiments in which the shunt 300 comprises only a single partially restrictive section, such as partially restrictive section 352, the remainder of the shunt 300 will be the main portion, which can have generally a constant cross-sectional area and/or profile. As such, by removing the portion 342, the flow resistance of the shunt 300 will decrease. Further, the flow value of the shunt 300 will increase.

Some embodiments of the method can be implemented such that only a portion of the partially restrictive section 352 is removed from the shunt 300. For example, the cutting device 340 can cut the shunt 300 such that half of the partially restrictive section 352 remains interconnected with the shunt 300. As such, although the flow resistance of the shunt 300 will decrease, the flow resistance will be higher than it otherwise would be if the entire partially restrictive section 352 were removed. Various implementations of methods can be performed such that more or less of a partially restrictive section(s) are removed during a modification procedure. Accordingly, a clinician can selectively tune the flow resistance or flow value of the shunt based on specific parameters or properties of the surrounding tissue and the shunt.

In accordance with some embodiments, the shunt can also be positioned such that the restrictive end thereof is positioned in the targeted space or location of lower pressure, such as in the subconjunctival space of the eye. For example, FIG. 10 illustrates a shunt 380 having a partially obstructive or flow-limiting restrictive section 382 in a restrictive end 384 thereof that is positioned in the subconjunctival space 320. In such implementations, the partially restrictive section 382 or restrictive end 384 of the shunt 380 can be manipulated to adjust the flow resistance or flow value of the shunt 380.

Similar to the embodiment discussed above in FIG. 9, a cutting device can be inserted into the subconjunctival space 320 in order to modify the restrictive end 384.

For example, the cutting device can be a needle that cuts at least a portion or shunt fragment 390 of the restrictive end 384 from the shunt 380. The cutting of the restrictive end 384 in the subconjunctival space 320 can be achieved through a needle manipulation of the shunt 380. This can be performed similar to a needling procedure, in which a 27GA or 30GA needle is entered under the conjunctiva within a few millimeters from the restrictive end 384. The tip of the needle can then be carefully advanced toward the restrictive end 384. Subsequently, through a cutting motion, the tip of the needle can then cut a shunt fragment 390 of the restrictive end 384 in order to adjust the flow resistance or flow value of the shunt 380. This needle procedure can also be performed at the slit lamp under topical numbing only. In some embodiments, such as that illustrated in FIG. 10, the entire partially restrictive section 382 can be severed from the shunt 300.

Referring now to FIG. 11, after the shunt 380 has been modified by the cutting device, the displaced or severed shunt fragment 390 of the shunt 380 can be removed from or repositioned within the subconjunctival space 320 in a position adjacent to a modified end 392 of the shunt 382. For example, the modified end 392 of the shunt 382 can be spaced apart from the shunt fragment 390 such that a small space or is present between the modified end 392 and the shunt fragment 390. In this manner, outflow through the modified end 392 can generally remain clear. In particular, the shunt fragment 390 can act as a spacer that will tend to prevent blockage and preserve outflow through the modified end 392. This can be particularly true for a shunt material that remains very quiet in the eye, such as a gelatin material. In some embodiments, the shunt fragment 390 can be spaced apart from the modified end 392 by from about 0.2 mm to about 2 mm. Further, the shunt fragment 390 can be spaced apart from the modified end 392 by from about 0.5 mm to about 1 mm.

Laser Modification of the Shunt

Figure 12:
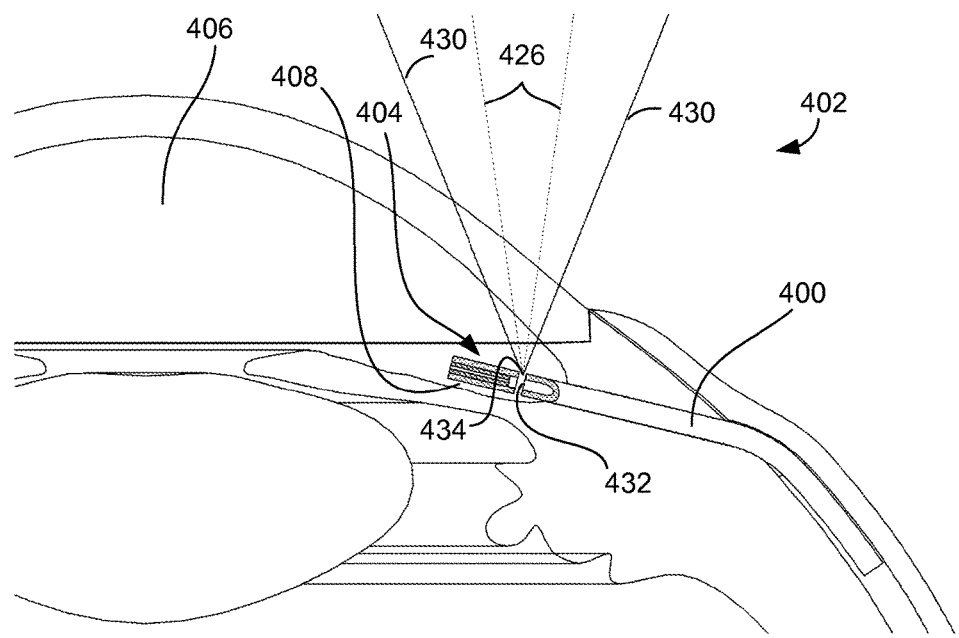
FIG. 12 illustrates the severance of a portion of the partially restrictive section of a shunt, oriented as illustrated in FIG. 8, using a laser, according to some embodiments.
Figure 13:
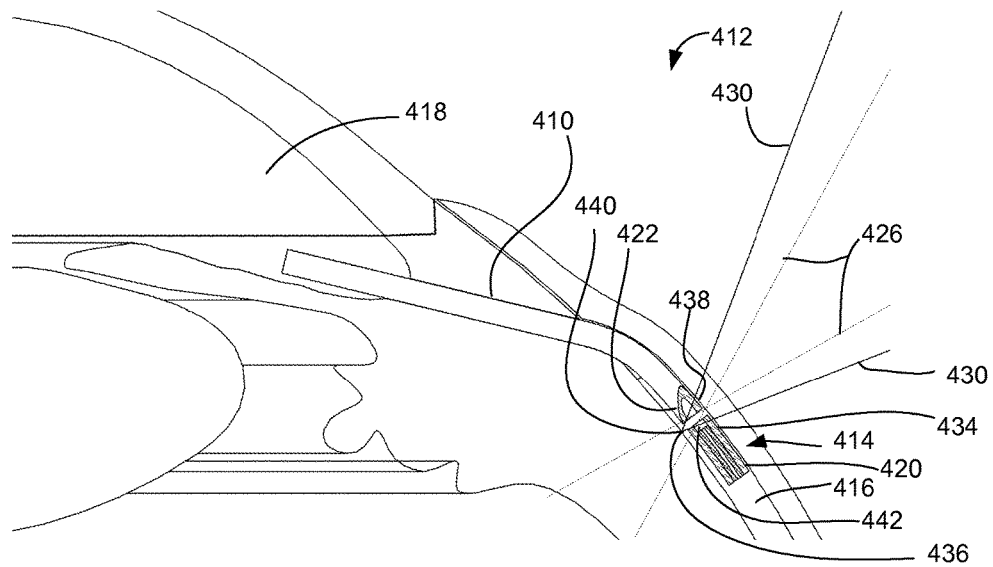
FIG. 13 illustrates the severance of a portion of the partially restrictive section of a shunt, oriented as illustrated in FIG. 10, using a laser, according to some embodiments.
Figure 14:
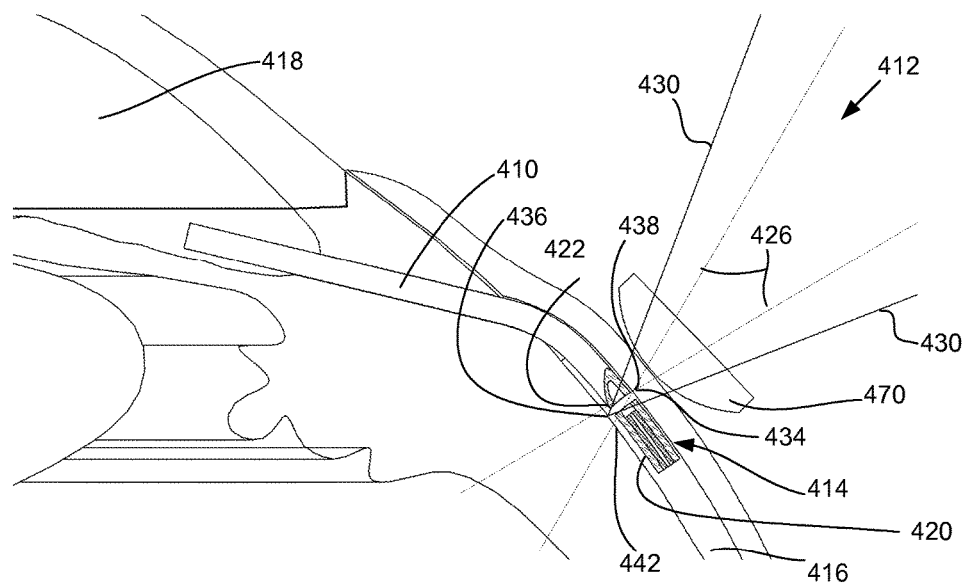
FIG. 14 illustrates the severance of a portion of the partially restrictive section of a shunt, oriented as illustrated in FIG. 11, using a laser and an optical lens, according to some embodiments.

Some embodiments of the shunts and methods disclosed herein can be provided such that the shunt can be modified using a laser procedure. FIGS. 12-14 illustrate aspects of methods in which a shunt is modified using a laser.

For example, FIG. 12 illustrates a method for modifying a shunt 400 implanted in an eye 402. While FIG. 12 illustrates that the shunt 400 can comprise a restrictive end 404 placed in an anterior chamber 406 of the eye 402, other implementations of methods can be provided in which a restrictive end is located in a targeted space or a location of lower pressure. For example, FIGS. 13-14 illustrate a method for modifying a shunt 410 in an eye 412, wherein the shunt 410 includes a restrictive end 414 disposed in a targeted space, shown as a subconjunctival space 416 and an opposing end that extends into an anterior chamber 418 of the eye 412.

Similar to the embodiments discussed above with respect FIGS. 9-11, the laser procedures for modifying the shunts 400, 410 can allow a clinician to at least partially cut and/or separate a shunt fragment from the partially obstructive or flow-limiting restrictive section of the shunt. The shunt fragment that is at least partially cut and/or separated from the shunt can be removed from the eye or left in place, as similarly discussed above (the details of which can also be implemented in laser embodiments). For example, in FIG. 12, a shunt fragment 408 that is separated from the restrictive end 404 of the shunt 400 can be extracted from the anterior chamber 406.

However, in FIGS. 13-14, a shunt fragment 420 that is separated from the shunt 410 can either be removed from the subconjunctival space 416 or positioned within the subconjunctival space 416 to act as a spacer, as discussed above with regard to FIG. 11. As similarly discussed above with respect to FIG. 11, after the shunt 410 has been modified by the laser, the displaced or separated shunt fragment 420 of the shunt 410 can be removed from or repositioned within the subconjunctival space 416 in a position adjacent to a modified end 422 of the shunt 410.

For example, the shunt fragment 420 can be spaced apart from the modified end 422 of the shunt 410 such that a small space or gap is present between the modified end 422 and the shunt fragment 420. In this manner, outflow through the modified end 422 can generally remain open and less restricted. The shunt fragment 420 can act as a spacer that will tend to prevent blockage, local fibrosis buildup and preserve outflow through the modified end 422. In some embodiments, the shunt can advantageously be fabricated from a material that remains very quiet in the eye, such as a gelatin material. The shunt fragment 420 can be spaced apart from the modified end 422 by from about 0.2 mm to about 2 mm. In some embodiments, the shunt fragment 420 can be spaced apart from the modified end 422 by from about 0.5 mm to about 1 mm.

In accordance with some methods, the laser procedure can be performed using one or more lasers to modify the configuration of the shunt. For example, the laser can comprise a surgical or treatment beam and an aiming beam. The modification or laser cutting can be achieved by using a single higher power laser or by crossing two or more lower power lasers. In some instances, the laser procedure can be implemented using two aiming beams that target a given location and then using one or more treatment beams to modify the shunt.

In some methods, the treatment beam(s) can be a photodisruptive YAG laser. The treatment beam(s) and the aiming beam(s) can also be used in a slit lamp configuration. For example, the laser implant cutting procedure can be performed by aligning a pair of aiming beams and then pulsing one or more YAG lasers in a slit lamp configuration to target and cut or modify the restrictive end of a shunt.

The treatment beam(s) can be pulsed at a wavelength of 532 nm, 635 nm, 808 nm, 940 nm, 1053 nm, 1064 nm, 1120 nm, 1320 nm, 1440 nm, and/or 1540 nm. In some embodiments, the wavelength can be 1064 nm.

The treatment beam(s) can be pulsed laser beam with a pulse duration of 1 ns to 1 ms, a pulse repetition rate from single shot to 100 Hz and a pulse energy from 0.2 mJ to 10 mJ. The pulse energy can be from about 2 mJ to about 6 mJ.

In some embodiments the pulse duration can be 3 ns and the pulse energy can be 3 mJ.

The laser focusing angle is from about 10 degrees to about 30 degrees. The focusing angle can be from about 14 degrees to about 20 degrees. Further, in some embodiments, the focusing angle can be about 16 degrees.

The treatment beam(s) can have a beam waist diameter or "spot size" of from about 1 µm to about 20 µm. The spot size can be from about 6 µm to about 15 µm. In some embodiments, the spot size can be about 8 µm.

According to some methods, two intersecting aiming beams (illustrated in FIGS. 12-14 as 426) can be overlapped at a target location. For example, in FIG. 12, the aiming beams 426 can be overlapped or crossed such that an overlap point or target location 432 of the beams lies on or targets a top surface 434 of the shunt 400 or conjuctival tissue above the shunt 400. In FIGS. 13 and 14, the aiming beams 426 can be overlapped or crossed at an overlap point or target location 438, which can be along the top surface 434 of the shunt 410. However, in various methods, the overlap points 432, 438 can be moved to another location as desired, such as along a bottom surface 442 of the shunt 410. When the aiming beams 426 are properly aligned, one or more additional lasers can be used to modify the shunt.

Further, while the overlap point or target location of the aiming beams 426 can be at a first location, the treatment beam(s) can be focused to a different point or second location. For example, the focus of the treatment beam(s) can be adjusted to be deeper past the overlap point or target location, to extend further to the tissue. The focus of the treatment beam(s) can be offset by a depth offset 440 (shown for example, in FIG. 13). The depth offset 440 can be a distance beyond the overlap point or target location where the laser beam is focused. While in some embodiments the depth offset 440 can be a depth as generally measured from the top or uppermost surface or edge of the shunt (when the overlap point or target location is at the top surface of the shunt), the depth offset 440 can also be generally measured from the bottom surface of the shunt (when the overlap point or target location is at the bottom surface of the shunt). The depth offset 440 can be from about 50 µm to about 400 µm. In some embodiments, the depth offset can be spaced at about 250 µm from the aiming beam intersection point.

According to some embodiments, the alignment of the treatment and aiming beam(s), as well as the firing of the treatment beam(s) is done with a manual slit lamp actuator and fire bottom. Such embodiments can provide sufficient precision to effectively implement the procedure.

With a proper alignment, the shunt 400, 410 can be modified (e.g., cut or broken) with a single shot at around 3 mJ pulse energy. According to some embodiments, a reliable/typical cutting can be achieved with 3-5 pulses placed in the same focal area with only minimal adjustments in between.

For example, as shown in FIG. 13, the aiming beams 426 can overlap at point 438 generally along the top surface 434 of a 300 µm diameter gelatin shunt 410. The aiming beams 430 can be focused at a depth offset of about 250 um, which will focus the beams deeper toward the bottom surface 442 of the shunt 410. In such embodiments, the intersecting aiming beams 430 will tend to be focused on the bottom surface 442 of the shunt 410, which will generally cause cracking and cutting of the shunt 410 from the bottom up. In this manner, any potential tissue damage of the conjunctiva above the shunt 410 (e.g., conjuctival perforations) can be avoided.

Additionally, in accordance with some methods, a lens 470 can be used to improve accuracy of the targeting. By improving the accuracy, a clinician can avoid hitting a blood vessel with a laser pulse and the visual obstruction that would result therefrom. Further, the use of a lens 470 can also help create a better optical beam entrance interface into the eye 412. In some methods, the lens 470 can be a small flat or plano-convex glass piece.

The lens 470 can be placed adjacent to the eye 412 near the location of the restrictive end 414 of the shunt 410. When placed adjacent to the eye 412, a convex side of the lens 470 can face down towards the conjunctiva/shunt. In some methods, the lens 470 can be pushed onto the area over the implant during the laser cutting. Thereafter, the treatment and aiming beam(s) can be utilized according to an implementation disclosed are taught herein.

Modification Through Dissolution

Additional methods and devices can also be provided in which a flow-tunable shunt provides early hypotony protection and a later, gradual lessening of the flow restriction without any post-op surgical intervention (such as the cutting above). In some embodiments, whether used independently of or in conjunction with other aspects of embodiments disclosed herein, the shunt can also comprise an unobstructive or unrestrictive main section and a partially obstructive, restrictive, or flow-limiting dissolvable plug or section. The main section and/or the restrictive section can also be detachable or separable from the shunt, as discussed in embodiments above.

The shunt can be configured such that flow can move more easily through the main section than through the partially restricted section. The main section can comprise a wall that defines a first flow cross-sectional area. The partially restrictive dissolvable section can comprise a wall that defines an aperture, lumen, or channel through which fluid can pass, but with greater resistance than through the main section. Thus, in some embodiments, the presence of a dissolvable section can slow, but not entirely restrict flow through the shunt. Instead, a dissolvable section can be located so as to restrict flow at early stages after the surgical procedure, but to dissolve over time, thereby increasing flow through the dissolvable section and hence, through the shunt.

In some embodiments, the shunt can comprise one or more partially restrictive dissolvable sections. For example, the shunt can comprise a partially restrictive dissolvable section at a single end thereof. The shunt can comprise two or more partially restrictive dissolvable sections, spaced close together or spaced apart from each other at opposing ends of the shunt. In some methods, a partially restrictive dissolvable section can be placed either in the anterior chamber or in an area of lower pressure, such as the subconjunctival space. An aspect of some embodiments is the realization that there may be an advantage to placing a dissolvable section in the anterior chamber (compared with having the dissolvable section only in the subconjunctival space) due to the possibility that particulate or debris could float into the shunt lumen and block flow through a dissolvable section in the subconjunctival space.

Further, the partially restrictive section(s) can comprise a wall that defines an aperture, lumen, or channel. As noted similarly with regard to other embodiments above, the wall of the partially restrictive section(s) can define a second flow cross-sectional area. The second flow cross-sectional area can be less than the first flow cross-sectional area of the main section. In some embodiments, the wall(s) can define aperture(s), lumen(s), or channel(s) that are generally tubular. Further, the aperture(s), lumen(s), or channel(s) can be square, polygonal, triangular, or other varieties of random shapes. The wall(s) can be configured such that the aperture(s), lumen(s), or channel(s) can extend along a central axis of the partially restrictive section(s). However, the aperture(s), lumen(s), or channel(s) can also extend longitudinally along the partially restrictive section while traversing and/or spaced apart from the central axis of the partially restrictive section. Further, the aperture(s), lumen(s), or channel(s) can be encircled by the material forming the partially restrictive section. However, the aperture(s), lumen(s), or channel(s) can also be formed intermediate the wall of the partially restrictive section and the wall of the main section.

Additionally, the material forming the partially restrictive dissolvable section(s) of the shunt can be configured to dissolve according to a desired dissolution rate, dissolution order, and/or dissolution pattern. A partially restrictive dissolvable section can comprise more than one type of material. The material(s) can be layered axially, circumferentially offset, or otherwise positioned to provide a differential or staged dissolution order or pattern. The material(s) can have variable or different dissolution rates.

Figure 15:
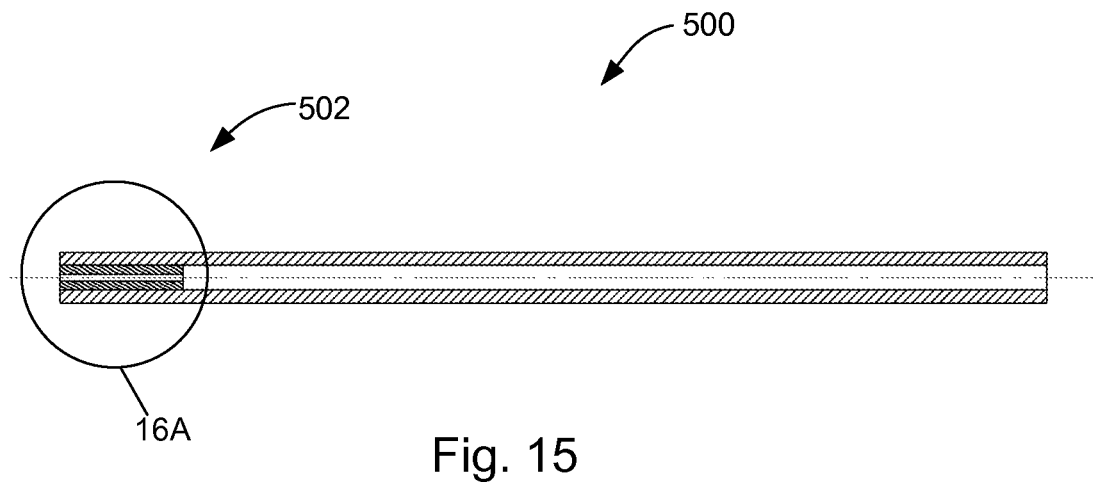
FIG. 15 illustrates an intraocular shunt having one or more dissolvable sections, according to some embodiments.

Referring to FIGS. 15-22, various embodiments of shunts having a partially restrictive section. FIG. 15 illustrates a shunt 500 having a first end 502. The first end 502 comprises a partially restrictive section 504. The partially restrictive section 504 can comprise a material that is loaded into a lumen 506, formed by a wall 508 of the shunt 500 or coated onto the shunt wall 508. For example, in some embodiments, the material of the partially restrictive section 504 can be formed by dipping the shunt 500, coating the shunt 500, laminating the shunt 500, layering the shunt 500 over the partially restrictive section 504, pushing a plug or tube of material into the shunt 500, or otherwise loading material onto the wall 508 or into the lumen 506.

Figure 16A:
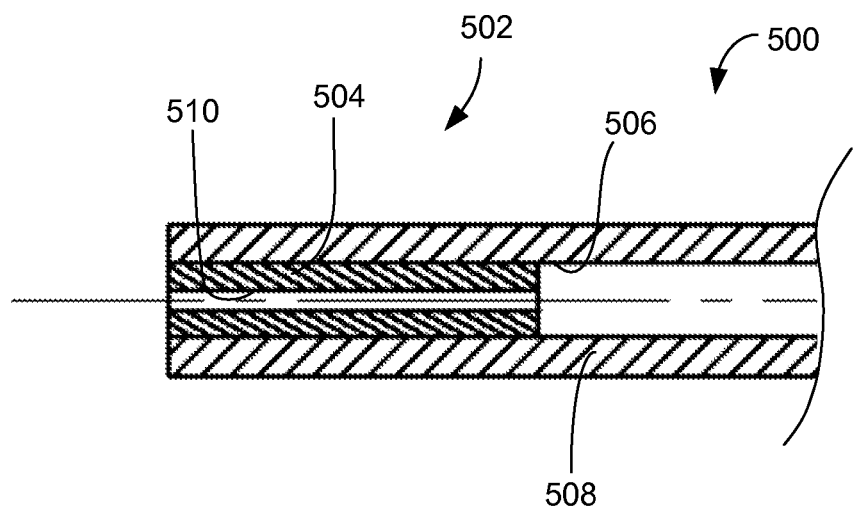
FIGS. 16A-22 illustrate cross-sectional views of an intraocular shunt having one or more dissolvable sections, according to some embodiments.
Figure 16B:
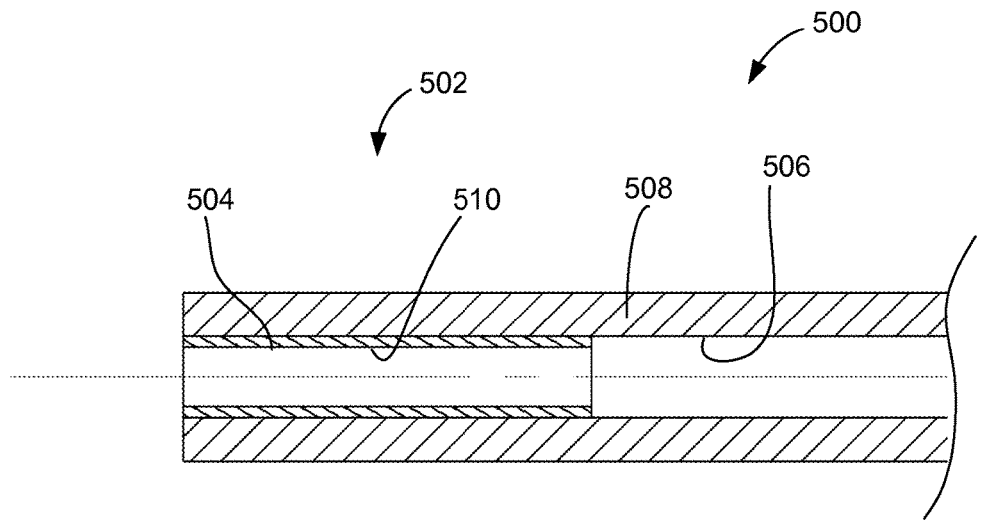

FIGS. 16A-B illustrate the first end 504 at different stages of dissolution. FIG. 16A illustrates an embodiment of the partially restrictive section 504 prior to implantation and dissolution. As illustrated generally, the partially restrictive section 504 comprises an aperture or channel 510 for allowing at least some fluid flow therethrough. Accordingly, for a short period after being installed, the shunt 500 will provide minimal flow therethrough, thus tending to avoid hypotony.

However, as shown in FIG. 16B, the partially restrictive section 504 can dissolve over time such that the aperture or channel 510 will increase in size, thus permitting greater flow therethrough. In some embodiments, as the section 504 dissolves, the aperture or channel 510 will tend to approximate or become generally the same dimension as the shunt wall 508. Such dissolution can tend to increase flow in order to compensate for later increased biological outflow restrictions.

Figure 17:
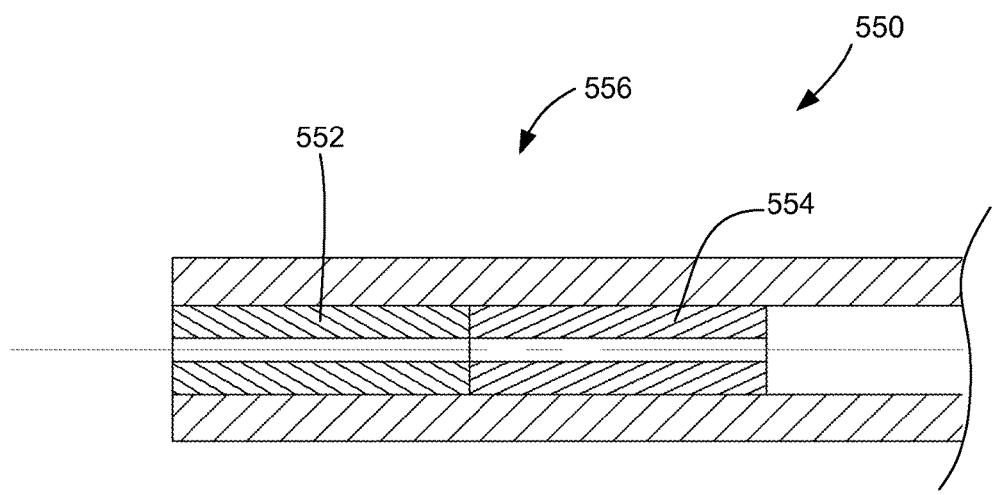
Figure 18:
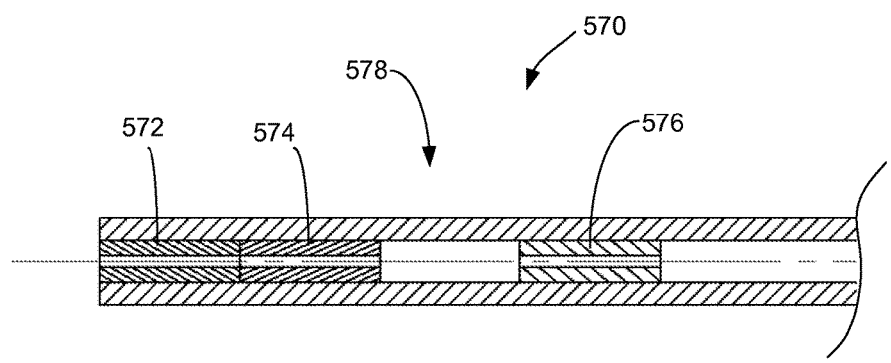
Figure 19:
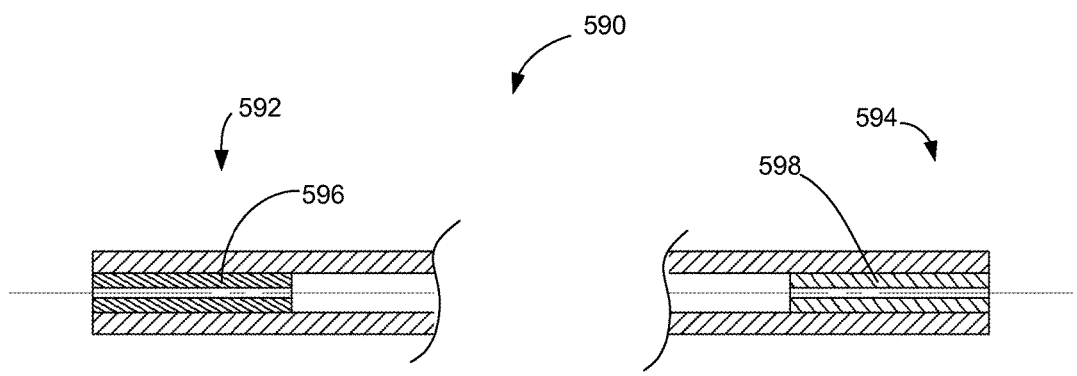

The embodiments shown in FIGS. 17-19 illustrate shunts having more than one partially restrictive section. These shunts can be configured to vary the number of partially restrictive sections, the length(s) of the partially restrictive section(s), the inner diameter or size of the apertures or channels of the partially restrictive section(s), the material used for each partially restrictive section, spacing relative to each other and the shunt, etc.

For example, FIG. 17 illustrates a shunt 550 having a pair of partially restrictive sections 552 and 554 positioned at a first end 556 of the shunt 550. The sections 552, 554 are positioned contiguously without a spaced therebetween. FIG. 18 illustrates another shunt 570 having partially restrictive sections 572, 574, 576 positioned adjacent to each other at a first end 578 of the shunt 570. While the sections 572, 574 are positioned contiguously, the section 576 is spaced apart from the other sections 572, 574. FIG. 19 illustrates yet another shunt 590 having first and second ends 592, 594. Each end 592, 594 comprises a partially restrictive section 596, 598.

Figure 20:
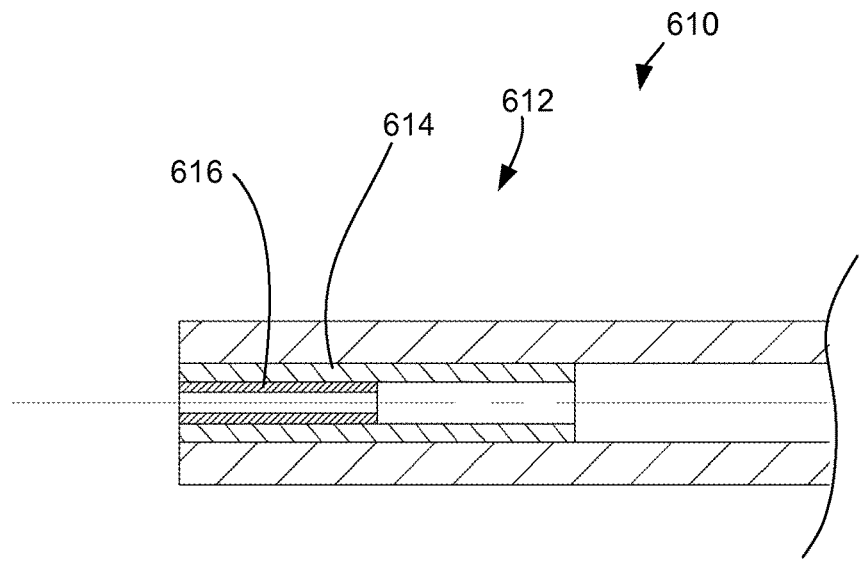
Figure 21:
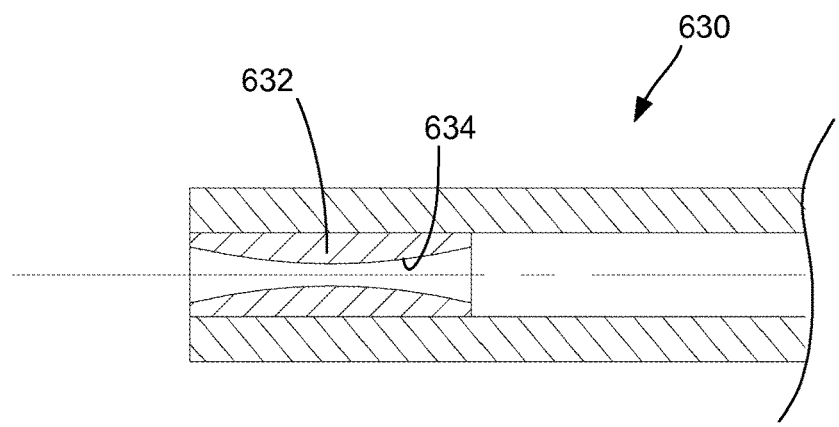
Figure 22:
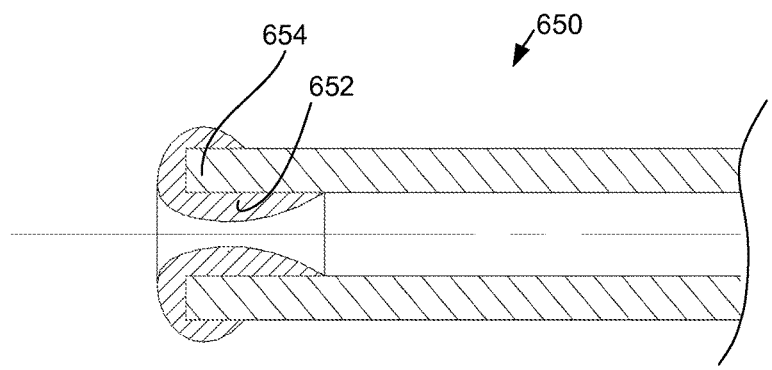

FIGS. 20-22 also illustrate possible aspects of some embodiments. For example, FIG. 20 illustrates a shunt 610 having a partially restrictive section 612. The partially restrictive section 612 can comprise axially nested layers 614, 616. FIG. 21 illustrates a shunt 630 having a partially restrictive section 632. The partially restrictive section 632 can have a variable diameter aperture or channel 634. Further, while some illustrated embodiments show that a partially restrictive section can extend only to the end of the shunt or only within the shunt lumen, FIG. 22 illustrates a shunt 650 having a partially restrictive section 652 that extends axially beyond an end 654 of the shunt 650. The embodiments of FIG. 22 can be formed by dipping the shunt end 654 into a desired material, for example. As such, various embodiments can comprise any of a variety of geometries.

Shunt Materials

All or only a portion of a shunt may be dissolvable. For example, the dissolvable section can comprise a dissolvable biocompatible material. The material can be configured to dissolve over a set or desired period of time, from days to months, based on how long hypotony protection is desired.

In some embodiments, the material selected for the shunt can be a gelatin or other similar material. In some embodiments, the gelatin used for making the shunt can be a gelatin Type B from bovine skin. A preferred gelatin is PB Leiner gelatin from bovine skin, Type B, 225 Bloom, USP. Another material that may be used in the making of the shunts is a gelatin Type A from porcine skin, also available from Sigma Chemical. Such gelatin is available is available from Sigma Chemical Company of St. Louis, Mo. under Code G-9382.

Still other suitable gelatins include bovine bone gelatin, porcine bone gelatin and human-derived gelatins. In addition to gelatins, microfistula shunt may be made of hydroxypropyl methycellulose (HPMC), collagen, polylactic acid, polylglycolic acid, hyaluronic acid and glycosaminoglycans.

The shunt material can be cross-linked. For example, when a gelatin is used, cross-linking can increase the inter- and intramolecular binding of the gelatin substrate. Any means for cross-linking the gelatin may be used. In some embodiments, the formed gelatin shunts can be treated with a solution of a cross-linking agent such as, but not limited to, glutaraldehyde. Other suitable compounds for cross-linking include 1-ethyl-3-[3-(dimethyamino)propyl]carbodiimide (EDC). Cross-linking by radiation, such as gamma or electron beam (e-beam) may be alternatively employed.

The dissolvable section can comprise a material that is identical, similar, or different from the material of the shunt. In some embodiments, the dissolvable section material can be made out of a gelatin, which can be similar to a gelatin used to make the shunt, with the gelatins differing in the amount of crosslinking each has undergone.

In some embodiments, the shunt can be cross-linked by contacting the shunt with a solution of about 25% glutaraldehyde for a selected period of time. One suitable form of glutaraldehyde is a grade 1G5882 glutaraldehyde available from Sigma Aldridge Company of Germany, although other glutaraldehyde solutions may also be used. The pH of the glutaraldehyde solution should preferably be in the range of 7 to 7.8 and, more preferably, 7.35-7.44 and typically about 7.4.+−.0.01. If necessary, the pH may be adjusted by adding a suitable amount of a base such as sodium hydroxide as needed.

For example, a "permanent" implant can be crosslinked by keeping it in a 25% Gluderaldehyde solution for 16 hours. This saturates the crosslinking and results in a permanent implant that does not dissolve over any meaningful time frame (e.g., 10 years). However, in such embodiments, a gelatin that has undergone much less crosslinking (using a lower crosslinking time and/or a lower Gluderaldehyde concentration) can be used for the dissolvable section. By lowering the crosslinking time and/or the amount of Gluderaldehyde concentration, less than complete crosslinking can be achieved, which results in a dissolving material over an adjustable time frame. Other dissolvable materials and other crosslinking techniques can be used to provide the dissolvable section.

According to some methods, by adjusting the Gluderaldehyde concentration, crosslinking time, crosslinking temperature and/or the geometry of the dissolvable section, the dissolving time can be from at least about 15 minutes to several years. The dissolving time can also be from at least about 1 hour to several months. For example, a completely non-crosslinked gelatin dissolvable section can dissolve in about 20 minutes. Therefore, the Gluderaldehyde concentration, crosslinking time, and/or the geometry (longitudinal length, aperture or channel size, etc.) of the dissolvable section can be modified accordingly to adjust the dissolution rate of the dissolvable section.

Regarding the design considerations for shunt inner dimension or diameter and length and dissolvable section length and channel dimensions, longer "pipes" have higher fluid resistance and fluid resistance decreases as "pipe" radius and cross-sectional area increase. Specifically, flow and resulting pressure values can be determined using formulas known in the art. The flow rate for flow through a tube having different interior cross sections can be calculated using such formulas. Calculating laminar flow through a tube can be performed using the Hagen-Poiseuille equation:

$$\Phi = \frac{dV}{dt} = v\pi R^2 = \frac{\pi R^4}{8\eta}\left(\frac{-\Delta P}{\Delta x}\right) = \frac{\pi R^4}{8\eta}\frac{|\Delta P|}{L}$$

In the above formula, $\Phi$ is the volumetric flow rate, V is a volume of the liquid poured (cubic meters), t is the time (seconds), V is mean fluid velocity along the length of the tube (meters/second), x is a distance in direction of flow (meters), R is the internal radius of the tube (meters), $\Delta P$ is the pressure difference between the two ends (pascals), $\eta$ is the dynamic fluid viscosity (pascal-second (Pa·s)), L is the total length of the tube in the x direction (meters). Assuming that the flow restriction of a large lumen shunt is insignificant, the pressure difference $\Delta P$ between the shunt entrance and exit is given by the length L and the inner diameter (radius R) of the plugged/constricted part of the shunt only.

Additionally, in accordance with some methods, the shunts of any of FIGS. 3-23 may be made by dipping a core or substrate such as a wire of a suitable diameter in a solution of material, such as gelatin. In some methods, in order to form shunts having one or more restrictive sections (e.g., dissolvable portions), a core or substrate can be configured to include one or more peaks, valleys, protrusions, and/or indentations corresponding to the desired inner profile of the shunt. The core or substrate can be coated or dipped multiple times in order to become coated with a desired number of layers or materials. For example, a core or substrate can have a first section having a small outer diameter and a second section having a large outer diameter. The section having a smaller outer diameter can be coated or dipped in a solution such that the outer diameter along the first section is generally equal to the large outer diameter of the second section. Thereafter, the first and second sections of the core or substrate can be immersed in a solution and dried. When removed, the shunt can therefore have an inner diameter that narrows in a restricted section thereof, which corresponds to the first section of the core or substrate. Other details and features of methods of preparing and fabricating a shunt are disclosed in U.S. Application Publication No. 2012/0197175, filed on Dec. 8, 2011 (AQUE-009/06US) and Ser. No. 13/314,939, filed on Dec. 8, 2011 (AQUE-015/00US), the entireties of each of which are incorporated herein by reference.

In the case of a gelatin implant, the solution can be prepared by dissolving a gelatin powder in de-ionized water or sterile water for injection and placing the dissolved gelatin in a water bath at a temperature of about 55° C. with thorough mixing to ensure complete dissolution of the gelatin. In one embodiment, the ratio of solid gelatin to water is about 10% to 50% gelatin by weight to 50% to 90% by weight of water. In some embodiments, the gelatin solution includes about 40% by weight, gelatin dissolved in water. The resulting gelatin solution preferably is devoid of any air bubbles and has a viscosity that is from about 200 cp (centipoise) to about 500 cp. The solution can also have a viscosity from about 260 to about 410 cp.

As discussed further herein, the gelatin solution may include biologics, pharmaceuticals, drugs, and/or other chemicals selected to regulate the body's response to the implantation of the shunt and the subsequent healing process. Examples of suitable agents include anti-mitolic pharmaceuticals such as Mitomycin-C or 5-Fluorouracil, anti- VEGF (such as Lucintes, Macugen, Avastin, VEGF or steroids), anti-coagulants, anti-metabolites, angiogenesis inhibitors, or steroids. By including the biologics, pharmaceuticals, drugs, or other chemicals in the liquid gelatin, the formed shunt will be impregnated with the biologics, pharmaceuticals, drugs, or other chemicals.

Drug-Eluting Shunts

In accordance with some embodiments, the shunt can comprise a drug or drug-eluting portion for drug delivery to one or more target locations within the eye. A drug-eluting portion can be provided in combination with any of the embodiments disclosed or taught herein. For example, shunts such as those illustrated in FIG. 3-14 or 15-22 can comprise a drug-eluting portion. Thus, some embodiments provide a shunt that also operates as a drug delivery device inside the eye.

One or more drugs can be carried by the shunt for delivery to the target location(s). The shunt itself can carry a drug and can be partially or completely dissolvable. For example, one or more drugs can be carried in one or more dissolvable coating(s) along a surface of the shunt. The drug-eluting dissolvable coating(s) can extend along the entire length or only a portion of the length of the shunt. The drug(s) can also be carried as a component of a dissolvable section, according to some embodiments. In some embodiments, a time controlled drug release can be achieved by configuring the dissolvable coating or portion to provide a desired dissolution rate. Such drug-eluting portion(s) of the shunt can therefore provide a drug delivery, even without aqueous flow.

Aspects related to embodiments of drug delivery shunts are discussed in co-pending U.S. Application Publication No. 2012/0197175, filed on Dec. 8, 2008 (AQUE-009/06US), the entirety of which is incorporated herein by reference.

Various types of drugs can be used, including, glaucoma drugs, steroids, other anti-inflammatory, antibiotics, dry eye, allergy, conjunctivitis, etc.

At least a section of the shunt can comprise one or more drugs to provide a drug-eluting portion. In some embodiments, one or more drugs can be provided along the entire length of the shunt. However, in some embodiments, one or more drugs can be provided along less than the entire shunt or along only a portion of the shunt. For example, a drug can be integrated into only one of the ends of the shunt to provide a single drug-eluting end which can be placed into the anterior chamber or location of lower pressure. Further, other than being formed along an end of the shunt, the drug-eluting portion can also be formed along an intermediate portion of the shunt. Accordingly, embodiments can provide a targeted drug release inside the anterior chamber, inside the sclera, and/or in the subconjuctival space, depending on the location and configuration of the drug-eluting portion(s).

In some embodiments, the shunt can comprise multiple drug-eluting portions, which can each be formed to provide different dissolving times and/or have different drugs embedded therein. Accordingly, in some embodiments, two or more drugs can be delivered simultaneously on independent release timings.

For example, the shunt can comprise multiple dissolvable sections, which can each be formed to provide different dissolving times and/or have different drugs embedded therein.

The shunt can also be implanted into the suprachoroidal space (which one end in the anterior chamber and the other end in the suprachoroidal space or with the entire shunt being completely suprachoroidal) with the ability to deliver drugs at either or both ends or along an intermediate portion thereof. Some methods can be implemented such that multiple shunts (with the same or different drugs and with the same or different release timings) can be implanted in different places (e.g., the subconjunctival space, the suprachoroidal space, the anterior chamber, etc.).

Figure 23:
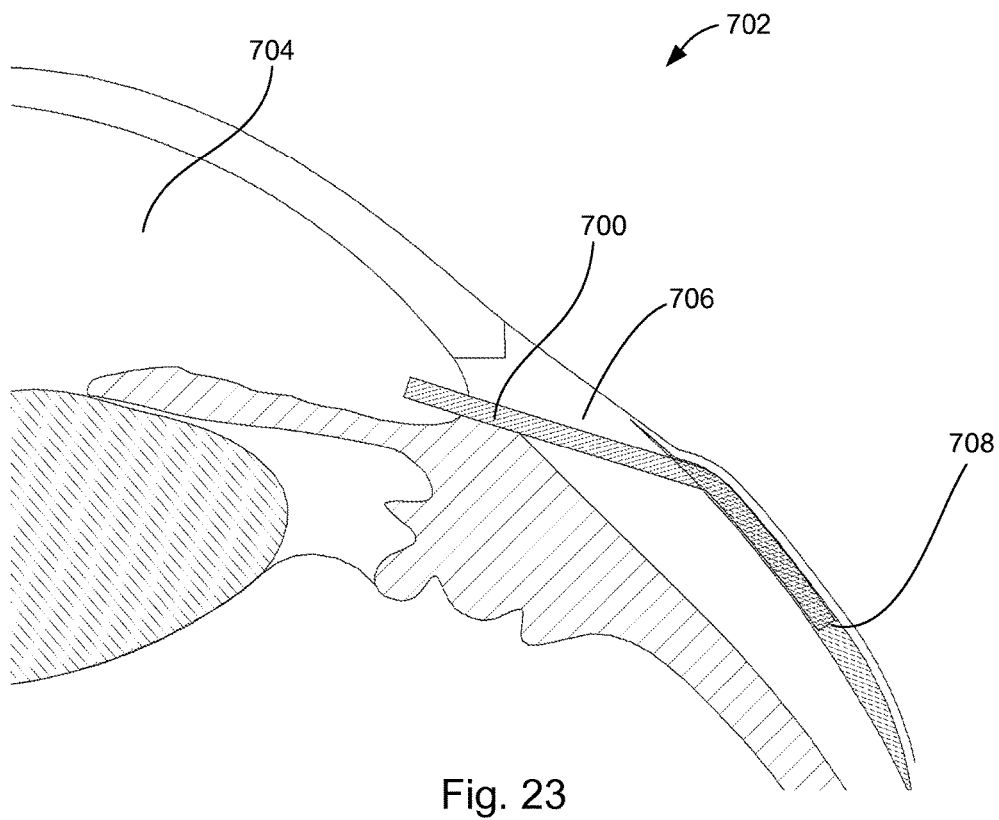
FIG. 23 illustrates placement of a drug-eluting intraocular shunt, according to some embodiments.

For example, referring to FIG. 23, a shunt 700 can be implanted into an eye 702. The shunt 700 can extend not only within an anterior chamber 704 of the eye 702, but also at least partially within the sclera 706 and the subconjunctival space 708. Accordingly, the opportunity is provided to configure the shunt 700 to comprise one or more drug-eluting portions to provide a targeted drug delivery to the anterior chamber 704, the sclera 706, the subconjunctival space 708, and/or other locations in the eye 702.

In the illustrated embodiment, a dissolvable coating can be placed onto the inner and/or outer surface of the shunt 700. Further, the shunt 700 can comprise one or more dissolvable sections positioned within a lumen of the shunt. Thus, one or more drugs can be delivered to one or more locations within the eye 702.

Tissue Compatible Shunts

In some embodiments, the shunt can comprise a material that has an elasticity modulus that is compatible with an elasticity modulus of tissue surrounding the shunt. For example, the intraocular shunt can be flexible, and have an elasticity modulus that is substantially identical to the elasticity modulus of the surrounding tissue in the implant site. As such, embodiments of the intraocular shunt can be easily bendable, may not erode or cause a tissue reaction, and may not migrate once implanted.

Accordingly, when implanted in the eye using an ab intern procedure, such as some methods described herein, embodiments of the intraocular shunt may not induce substantial ocular inflammation such as subconjunctival blebbing or endophthalmitis. Additional exemplary features of embodiments of the intraocular shunt are discussed in further detail below. In this manner, embodiments of the shunt can be configured to have a flexibility compatible with the surrounding tissue, allowing the shunt to remain in place after implantation without the need for any type of anchor that interacts with the surrounding tissue. Consequently, some embodiments of the shunt can thereby maintain fluid flow away from an anterior chamber of the eye after implantation without causing irritation or inflammation to the tissue surrounding the eye.

As discussed in applicant's co-pending application, U.S. application Ser. No. 13/314,939, filed on Dec. 8, 2011 (AQUE-015/00US), the entirety of which is incorporated herein by reference, elastic modulus or the modulus of elasticity, is a mathematical description of an object or substance's tendency to be deformed elastically when a force is applied to it. See also Gere (Mechanics of Materials, 6th Edition, 2004, Thomson) (the content of which is incorporated by reference herein in its entirety). The elasticity modulus of a body tissue can be determined by one of skill in the art. See, e.g., Samani et al. (Phys. Med. Biol. 48:2183, 2003); Erkamp et al. (Measuring The Elastic Modulus Of Small Tissue Samples, Biomedical Engineering Department and Electrical Engineering and Computer Science Department University of Michigan Ann Arbor, Mich. 48109-2125; and Institute of Mathematical Problems in Biology Russian Academy of Sciences, Pushchino, Moscow Region 142292 Russia); Chen et al. (IEEE Trans. Ultrason. Ferroelec. Freq. Control 43:191-194, 1996); Hall, (In 1996 Ultrasonics Symposium Proc., pp. 1193-1196, IEEE Cat.

No. 96CH35993, IEEE, New York, 1996); and Parker (Ultrasound Med. Biol. 16:241-246, 1990), the contents of each of which are incorporated by reference herein in its entirety.

The elasticity modulus of tissues of different organs is known in the art. For example, Pierscionek et al. (Br J Ophthalmol, 91:801-803, 2007) and Friberg (Experimental Eye Research, 473:429-436, 1988), both incorporated by reference herein in their entirety, show the elasticity modulus of the cornea and the sclera of the eye. Chen, Hall, and Parker show the elasticity modulus of different muscles and the liver. Erkamp shows the elasticity modulus of the kidney.

In some embodiments, the shunt can comprise a material that has an elasticity modulus that is compatible with the elasticity modulus of tissue in the eye, particularly scleral tissue. In certain embodiments, compatible materials are those materials that are softer than scleral tissue or marginally harder than scleral tissue, yet soft enough to prohibit shunt migration. The elasticity modulus for anterior scleral tissue is about $2.9 \pm 1.4 \times 10^6$ N/m2, and $1.8 \pm 1.1 \times 106$ N/m2 for posterior scleral tissue. In some embodiments, the material can comprise a gelatin. In some embodiments, the gelatin can comprise a cross-linked gelatin derived from Bovine or Porcine Collagen. Further, the shunt can comprise one or more biocompatible polymers, such as polycarbonate, polyethylene, polyethylene terephthalate, polyimide, polystyrene, polypropylene, poly(styrene-b-isobutylene-b-styrene), or silicone rubber.

Optional Shunt Features

As discussed in Applicant's co-pending application, U.S. application Ser. No. 13/314,939, filed on Dec. 8, 2011 (AQUE-015/00US), and in U.S. Application Publication No. 2012/0197175, filed Dec. 8, 2011 (AQUE-009/06US), the entireties of each of which is incorporated herein by reference, some embodiments of the shunt can comprise optional features. For example, some embodiments can comprise a flexible material that is reactive to pressure, i.e., the dimension or diameter of the flexible portion of the shunt fluctuates depending upon the pressures exerted on that portion of the shunt. Further, the shunt can comprise one or more side ports. Additionally, embodiments of the shunt can also comprise overflow ports. Some embodiments of the shunt can also comprise one or more prongs at an end thereof in order to facilitate conduction of fluid flow away from an organ. In accordance with some embodiments, the shunt can also be configured such that an end of the shunt includes a longitudinal slit. Other variations and features of the shunt can be incorporated into embodiments disclosed herein.

In addition to providing a safe and efficient way to relieve intraocular pressure in the eye, it has been observed that implanted shunts disclosed herein can also contribute to regulating the flow rate (due to resistance of the lymphatic outflow tract) and stimulate growth of functional drainage structures between the eye and the lymphatic and/or venous systems. These drainage structures evacuate fluid from the subconjunctiva which also result in a low diffuse bleb, a small bleb reservoir or no bleb whatsoever.

The formation of drainage pathways formed by and to the lymphatic system and/or veins may have applications beyond the treatment of glaucoma. Thus, the methods of shunt implantation may be useful in the treatment of other tissues and organs where drainage may be desired or required.

In addition, it has been observed that as a fully dissolvable shunt absorbs, a "natural" microfistula shunt or pathway lined with cells is formed. This "natural" shunt is stable. The implanted shunt stays in place (thereby keeping the opposing sides of the formed shunt separated) long enough to allow for a confluent covering of cells to form. Once these cells form, they are stable, thus eliminating the need for a foreign body to be placed in the formed space.

Deployment Devices

Deployment into the eye of an intraocular shunt according to this disclosure can be achieved using a hollow shaft configured to hold the shunt, as described herein. The hollow shaft can be coupled to a deployment device or part of the deployment device itself. Deployment devices that are suitable for deploying shunts according to the invention include, but are not limited to the deployment devices described in U.S. Pat. No. 6,007,511, U.S. Pat. No. 6,544,249, and U.S. Publication No. US2008/0108933, the contents of each of which are incorporated herein by reference in their entireties. In other embodiments, the deployment devices can include devices such as those as described in co-pending and co-owned U.S. patent application Ser. No. 12/946,222, filed on Nov. 15, 2010, U.S. patent application Ser. No. 12/946,645, filed on Nov. 15, 2010, and co-pending U.S. application Ser. No. 13/314,939, filed on Dec. 8, 2011 (AQUE-015/00US), the contents of each of which are incorporated by reference herein in their entireties.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

What is claimed is:

1. A method of adjusting a flow rate of an intraocular shunt implanted in an eye, the method comprising:
   determining a position of the shunt, the shunt having an open inlet end positioned in an anterior chamber of the eye and an open outlet end positioned in a location of lower pressure of the eye to permit aqueous humor to drain from the anterior chamber through the shunt; and
   after determining the position, cutting off a tubular section of the open outlet end to separate the tubular section from the shunt, thereby increasing flow through the shunt.

2. The method of claim 1, further comprising:
   determining an intraocular pressure of the eye;
   determining a target pressure drop necessary to achieve normal intraocular pressure; and
   determining a target longitudinal length of the shunt based on the target pressure drop;
   wherein the cutting comprises cutting the shunt to the target length.

3. The method of claim 2, further comprising separating the tubular section from the shunt.

4. The method of claim 2, further comprising removing the tubular section from the eye.

5. The method of claim 2, wherein the shunt comprises a tapered lumen.

6. The method of claim 1, wherein the shunt has a partially restrictive section and a main section, the partially restrictive section having a cross-sectional area less than a cross-sectional area of the main section, and wherein the tubular section is cut from the partially restrictive section and has a longitudinal length less than a longitudinal length of the partially restrictive section.

7. The method of claim 1, wherein the implanted shunt provides a non-zero flow rate before the tubular section of the shunt is cut off, and wherein the cutting off a tubular section increases flow through the shunt from the non-zero flow rate.

8. A method of adjusting a flow rate of an intraocular shunt implanted in an eye, the method comprising:
   determining a position of the shunt, the shunt having a main section extending from an anterior chamber of the eye toward a location of lower pressure of the eye, the shunt having an open-ended partially restrictive section positioned in the location of lower pressure of the eye, the partially restrictive section being dimensioned to have a first inner cross-sectional dimension, the main section being dimensioned to have a second inner cross-sectional dimension; and
   after determining the position, cutting off at least a tubular section of the open-ended partially restrictive section from the main section such that the flow rate through the shunt increases.

9. The method of claim 8, wherein the first inner cross-sectional dimension is less than the second inner cross-sectional dimension.

10. The method of claim 8, wherein a ratio of an inner diameter to an axial length of the main section is less than a ratio of an inner diameter to an axial length of the partially restrictive section.

11. The method of claim 8, wherein the cutting comprises removing the tubular section of the shunt, the tubular section of the shunt having a smaller diameter lumen than the main section.

12. The method of claim 8, wherein the cutting comprises cutting the shunt using a mechanical device.

13. The method of claim 8, wherein the cutting comprises cutting the shunt using a laser.

14. The method of claim 8, further comprising removing the tubular section from the eye after cutting the tubular section from the shunt.

15. The method of claim 8, further comprising leaving the tubular section in the eye after separating the tubular section from the shunt.

16. The method of claim 8, wherein separating the tubular section comprises removing the tubular section from the eye and leaving a portion of the partially restrictive section attached to the shunt.

17. The method of claim 8, further comprising:
   determining an intraocular pressure of the eye;
   determining a target pressure drop necessary to achieve normal intraocular pressure; and
   determining a target longitudinal length of the partially restrictive section based on the target pressure drop;
   wherein the cutting comprises cutting the partially restrictive section to the target length.

18. The method of claim 17, wherein the shunt comprises a tapered lumen.

19. The method of claim 8, wherein the cutting comprises cutting an entirety of the restrictive section from the main section.

20. The method of claim 8, wherein the implanted shunt provides a non-zero flow rate before the tubular section of the shunt is cut off, and wherein the cutting off at least a tubular section increases flow through the shunt from the non-zero flow rate.

21. A method of adjusting a flow rate of an intraocular shunt implanted in an eye, the method comprising:
   determining an intraocular pressure of the eye;
   determining a target pressure drop necessary to achieve normal intraocular pressure in the eye, the shunt being implanted in the eye and extending between an open inlet end positioned in an anterior chamber of the eye and an open outlet end positioned in a location of lower pressure of the eye;
   determining a target length of the shunt based on the target pressure drop; and
   after determining the target length, cutting off a tubular portion of the open outlet end of the shunt to cut the shunt to the target length.

22. The method of claim 21, further comprising separating the tubular portion from the shunt.

23. The method of claim 21, further comprising removing the tubular portion from the eye.

24. The method of claim 21, wherein the implanted shunt provides a non-zero flow rate before the tubular portion of the shunt is cut off, and wherein the cutting off a tubular portion increases flow through the shunt from the non-zero flow rate.

* * * * *